US012648804B2

(12) United States Patent
Babkin et al.

(10) Patent No.: US 12,648,804 B2
(45) Date of Patent: *Jun. 9, 2026

(54) ENDOVASCULAR NEAR CRITICAL FLUID BASED CRYOABLATION CATHETER AND RELATED METHODS

(71) Applicant: Adagio Medical, Inc., Laguna Hills, CA (US)

(72) Inventors: Alexei V. Babkin, Dana Point, CA (US); Steven W. Kovalcheck, San Diego, CA (US); Xiaoyu Yu, Laguna Hills, CA (US)

(73) Assignee: Adagio Medical, Inc., Laguna Hills, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 18/389,697

(22) Filed: Dec. 19, 2023

(65) Prior Publication Data

US 2024/0122636 A1     Apr. 18, 2024

Related U.S. Application Data

(60) Continuation of application No. 17/508,684, filed on Oct. 22, 2021, now Pat. No. 11,883,085, which is a
(Continued)

(51) Int. Cl.
*A61B 18/02*        (2006.01)
*A61B 18/00*        (2006.01)

(52) U.S. Cl.
CPC .... *A61B 18/02* (2013.01); *A61B 2018/00023* (2013.01); *A61B 2018/00351* (2013.01);
(Continued)

(58) Field of Classification Search
CPC .......... A61B 18/02; A61B 2018/00023; A61B 2018/00351; A61B 2018/00357;
(Continued)

(56) References Cited

U.S. PATENT DOCUMENTS 3,062,017 A     11/1962    Balcar et al.
3,613,689 A     10/1971    Crump et al.
(Continued)

FOREIGN PATENT DOCUMENTS

GB          1422535 A      1/1976
GB          2283678 A      5/1995
(Continued)

OTHER PUBLICATIONS

Arai, Y., et al., "Supercritical Fluids," pp. 161 and 199, ISBN 3540412484, Springer 2002.
(Continued)

*Primary Examiner* — Ankit D Tejani
*Assistant Examiner* — Joshua Brendon Solomon
(74) *Attorney, Agent, or Firm* — Batt IP A Law Corporation; Richard Batt

(57)        ABSTRACT

An endovascular near critical fluid based cryoablation catheter for creating an elongated lengthwise-continuous lesion in tissue can comprise an elongated shaft, a flexible distal tissue treatment section, and a distal tip. A plurality of flexible tubes can extend through the distal treatment section to transport a near critical fluid to and from the distal tip. The distal treatment section can also include a flexible fluid-sealed cover or barrier layer surrounding the delivery tubes. The cover and tubes can collectively define a space which is filled with a fluidic thermally conductive media. The thermally conductive media, fluid delivery tubes, and the cover can be arranged such that a flow of the near critical fluid through the tube bundle transfers heat between a target tissue and the distal treatment section of the catheter thereby creating the elongated lengthwise-continuous lesion in the tissue.

10 Claims, 28 Drawing Sheets

Related U.S. Application Data continuation of application No. 16/858,624, filed on Apr. 25, 2020, now Pat. No. 11,179,186, which is a division of application No. 14/915,631, filed as application No. PCT/US2014/056839 on Sep. 22, 2014, now Pat. No. 10,667,854.

(60) Provisional application No. 61/881,769, filed on Sep. 24, 2013.

(52) U.S. Cl.
CPC .............. *A61B 2018/00357* (2013.01); *A61B 2018/00577* (2013.01); *A61B 2018/0212* (2013.01); *A61B 2018/0262* (2013.01)

(58) Field of Classification Search
CPC .. A61B 2018/00577; A61B 2018/0212; A61B 2018/0262
See application file for complete search history.

(56) References Cited

U.S. PATENT DOCUMENTS

| | | | |
|---|---|---|---|
| 3,889,680 A | 6/1975 | Armao | |
| 3,942,010 A | 3/1976 | Peterson et al. | |
| 3,993,123 A | 11/1976 | Chu et al. | |
| 4,034,251 A | 7/1977 | Haas | |
| 4,167,771 A | 9/1979 | Simons | |
| 4,226,281 A | 10/1980 | Chu | |
| 4,281,268 A | 7/1981 | Sawa et al. | |
| 4,384,360 A | 5/1983 | Kitadate et al. | |
| 4,418,421 A | 11/1983 | Kitadate et al. | |
| 4,519,389 A | 5/1985 | Gudkin et al. | |
| 4,548,045 A | 10/1985 | Altares et al. | |
| 4,802,475 A | 2/1989 | Weshahy | |
| 4,838,041 A | 6/1989 | Bellows et al. | |
| 4,843,446 A | 6/1989 | Nishino et al. | |
| 4,945,562 A | 7/1990 | Staub | |
| 4,946,460 A | 8/1990 | Merry et al. | |
| 4,982,080 A | 1/1991 | Wilson et al. | |
| 5,012,505 A | 4/1991 | Zupancic et al. | |
| 5,037,395 A | 8/1991 | Spencer | |
| 5,108,390 A | 4/1992 | Potocky et al. | |
| 5,147,355 A | 9/1992 | Friedman et al. | |
| 5,147,538 A | 9/1992 | Wright et al. | |
| 5,155,093 A | 10/1992 | Den et al. | |
| 5,173,606 A | 12/1992 | Weinberger et al. | |
| 5,211,646 A | 5/1993 | Alperovich et al. | |
| 5,212,626 A | 5/1993 | Bell et al. | |
| 5,214,925 A | 6/1993 | Hoy et al. | |
| 5,237,824 A | 8/1993 | Pawliszyn | |
| 5,254,116 A | 10/1993 | Baust et al. | |
| 5,274,237 A | 12/1993 | Gallagher et al. | |
| RE34,502 E | 1/1994 | Webster, Jr. | |
| 5,275,595 A | 1/1994 | Dobak | |
| 5,324,286 A | 6/1994 | Fowle | |
| 5,334,181 A | 8/1994 | Rubinsky et al. | |
| 5,369,384 A | 11/1994 | Heins | |
| 5,400,602 A | 3/1995 | Chang et al. | |
| 5,405,533 A | 4/1995 | Hazlebeck et al. | |
| 5,417,072 A | 5/1995 | Silver et al. | |
| 5,433,717 A | 7/1995 | Rubinsky et al. | |
| 5,452,582 A | 9/1995 | Longsworth | |
| 5,471,844 A | 12/1995 | Levi | |
| 5,494,039 A | 2/1996 | Onik et al. | |
| 5,504,924 A | 4/1996 | Ohashi et al. | |
| 5,520,682 A | 5/1996 | Baust et al. | |
| 5,531,742 A | 7/1996 | Barken | |
| 5,573,532 A | 11/1996 | Chang et al. | |
| 5,603,221 A | 2/1997 | Maytal | |
| 5,661,980 A | 9/1997 | Gallivan | |
| 5,702,435 A | 12/1997 | Maytal | |
| 5,716,353 A | 2/1998 | Matsuura et al. | |
| 5,733,280 A | 3/1998 | Avitall | |
| 5,741,248 A | 4/1998 | Stern et al. | |
| 5,757,885 A | 5/1998 | Yao et al. | |
| 5,800,487 A | 9/1998 | Mikus et al. | |
| 5,800,488 A | 9/1998 | Crockett | |
| 5,816,052 A | 10/1998 | Foote et al. | |
| 5,885,276 A | 3/1999 | Ammar et al. | |
| 5,899,897 A | 5/1999 | Rabin et al. | |
| 5,899,898 A | 5/1999 | Arless et al. | |
| 5,899,899 A | 5/1999 | Arless et al. | |
| 5,901,783 A | 5/1999 | Dobak et al. | |
| 5,910,104 A | 6/1999 | Dobak et al. | |
| 5,916,212 A | 6/1999 | Baust et al. | |
| 5,924,975 A | 7/1999 | Goldowsky | |
| 5,947,960 A | 9/1999 | Griswold | |
| 5,950,444 A | 9/1999 | Matsunaga | |
| 5,954,714 A | 9/1999 | Saadat et al. | |
| 5,957,963 A | 9/1999 | Dobak | |
| 5,978,697 A | 11/1999 | Maytal et al. | |
| 5,993,444 A | 11/1999 | Ammar et al. | |
| 5,997,781 A | 12/1999 | Nishikawa et al. | |
| 6,004,269 A | 12/1999 | Crowley et al. | |
| 6,039,730 A | 3/2000 | Rabin et al. | |
| 6,074,412 A | 6/2000 | Mikus et al. | |
| 6,096,068 A | 8/2000 | Dobak et al. | |
| 6,106,518 A | 8/2000 | Wittenberger et al. | |
| 6,123,699 A | 9/2000 | Webster, Jr. | |
| 6,129,704 A | 10/2000 | Forman et al. | |
| 6,139,544 A | 10/2000 | Mikus et al. | |
| 6,142,991 A | 11/2000 | Schatzberger | |
| 6,161,543 A | 12/2000 | Cox et al. | |
| 6,171,277 B1 | 1/2001 | Ponzi | |
| 6,179,831 B1 | 1/2001 | Bliweis | |
| 6,182,666 B1 | 2/2001 | Dobak | |
| 6,190,378 B1 | 2/2001 | Jarvinen | |
| 6,190,382 B1 | 2/2001 | Ormsby et al. | |
| 6,193,644 B1 | 2/2001 | Dobak et al. | |
| 6,198,974 B1 | 3/2001 | Webster, Jr. | |
| 6,235,018 B1 | 5/2001 | LePivert | |
| 6,237,355 B1 | 5/2001 | Li | |
| 6,241,722 B1 | 6/2001 | Dobak et al. | |
| 6,251,105 B1 | 6/2001 | Mikus et al. | |
| 6,263,046 B1 | 7/2001 | Rogers | |
| 6,270,493 B1 | 8/2001 | Lalonde et al. | |
| 6,307,916 B1 | 10/2001 | Rogers et al. | |
| 6,324,852 B1 | 12/2001 | Cheng | |
| 6,341,629 B1 | 1/2002 | Clark et al. | |
| 6,347,675 B1 | 2/2002 | Kollé | |
| 6,355,029 B1 | 3/2002 | Joye et al. | |
| 6,368,304 B1 | 4/2002 | Aliberto et al. | |
| 6,377,659 B1 | 4/2002 | Snyder et al. | |
| 6,396,901 B1 | 5/2002 | Hell et al. | |
| 6,432,174 B1 | 8/2002 | Heung | |
| 6,440,126 B1 | 8/2002 | Abboud et al. | |
| 6,451,011 B2 | 9/2002 | Tu | |
| 6,471,694 B1 | 10/2002 | Kudaravalli et al. | |
| 6,471,696 B1 | 10/2002 | Berube et al. | |
| 6,475,212 B2 | 11/2002 | Dobak et al. | |
| 6,477,231 B2 | 11/2002 | Snyder et al. | |
| 6,486,078 B1 | 11/2002 | Rangarajan et al. | |
| 6,520,933 B1 | 2/2003 | Evans et al. | |
| 6,527,765 B2 | 3/2003 | Kelman et al. | |
| 6,530,420 B1 | 3/2003 | Takada et al. | |
| 6,537,271 B1 | 3/2003 | Murray et al. | |
| 6,544,176 B2 | 4/2003 | Mikus et al. | |
| 6,551,309 B1 | 4/2003 | LePivert | |
| 6,554,797 B1 | 4/2003 | Worthen | |
| 6,572,610 B2 | 6/2003 | Kovalcheck et al. | |
| 6,584,332 B2 | 6/2003 | Yoshitake et al. | |
| 6,592,581 B2 | 7/2003 | Bowe | |
| 6,602,276 B2 | 8/2003 | Dobak et al. | |
| 6,613,046 B1 | 9/2003 | Jenkins et al. | |
| 6,622,494 B1 | 9/2003 | Pourrahimi | |
| 6,622,507 B2 | 9/2003 | Cotte et al. | |
| 6,628,002 B2 | 9/2003 | Ritz et al. | |
| 6,648,879 B2 | 11/2003 | Joye et al. | |
| 6,685,720 B1 | 2/2004 | Wu et al. | |
| 6,706,037 B2 | 3/2004 | Zvuloni et al. | |
| 6,726,653 B2 | 4/2004 | Noda et al. | |
| 6,737,225 B2 | 5/2004 | Miller | |
| 6,746,445 B2 | 6/2004 | Abboud et al. | |

(56)　　　　References Cited

U.S. PATENT DOCUMENTS

| | | | |
|---|---|---|---|
| 6,767,346 B2 | 7/2004 | Damasco et al. | |
| 6,771,996 B2 | 8/2004 | Bowe et al. | |
| 6,776,765 B2 | 8/2004 | Soukup et al. | |
| 6,812,464 B1 | 11/2004 | Sobolewski et al. | |
| 6,848,458 B1 | 2/2005 | Shrinivasan et al. | |
| 6,848,502 B2 | 2/2005 | Bishop et al. | |
| 6,893,419 B2 | 5/2005 | Noda et al. | |
| 6,893,433 B2 | 5/2005 | Lentz | |
| 6,905,492 B2 | 6/2005 | Zvuloni et al. | |
| 6,905,493 B2 | 6/2005 | Lentz | |
| 6,936,045 B2 | 8/2005 | Yu et al. | |
| 6,941,953 B2 | 9/2005 | Feld et al. | |
| 6,984,230 B2 | 1/2006 | Scheller et al. | |
| 6,989,009 B2 | 1/2006 | Lafontaine | |
| 7,004,937 B2 | 2/2006 | Lentz et al. | |
| 7,013,170 B2 | 3/2006 | Bowe | |
| 7,022,120 B2 | 4/2006 | Lafontaine | |
| 7,083,612 B2 | 8/2006 | Littrup et al. | |
| 7,110,506 B2 | 9/2006 | Radley et al. | |
| 7,160,290 B2 | 1/2007 | Eberl et al. | |
| 7,195,625 B2 | 3/2007 | Lentz | |
| 7,220,252 B2 | 5/2007 | Shah | |
| 7,220,257 B1 | 5/2007 | Lafontaine | |
| 7,258,161 B2 | 8/2007 | Cosley et al. | |
| 7,273,479 B2 | 9/2007 | Littrup et al. | |
| 7,410,484 B2 | 8/2008 | Littrup et al. | |
| 7,507,233 B2 | 3/2009 | Littrup et al. | |
| 7,648,497 B2 | 1/2010 | Lane et al. | |
| 7,740,627 B2 | 6/2010 | Gammie et al. | |
| 7,758,571 B2 | 7/2010 | Saadat | |
| 7,842,031 B2 | 11/2010 | Abboud et al. | |
| 7,921,657 B2 | 4/2011 | Littrup et al. | |
| 8,012,147 B2 | 9/2011 | Lafontaine | |
| 8,177,780 B2 | 5/2012 | Cox et al. | |
| 8,298,217 B2 | 10/2012 | Lane et al. | |
| 8,387,402 B2 | 3/2013 | Littrup et al. | |
| 8,475,441 B2 | 7/2013 | Babkin et al. | |
| 8,491,520 B2 | 7/2013 | Smith et al. | |
| 8,591,503 B2 | 11/2013 | Littrup et al. | |
| 8,641,704 B2 | 2/2014 | Werneth et al. | |
| 8,679,104 B2 | 3/2014 | Abboud et al. | |
| 8,685,014 B2 | 4/2014 | Babkin et al. | |
| 8,740,891 B2 | 6/2014 | Babkin et al. | |
| 8,740,892 B2 | 6/2014 | Babkin et al. | |
| 8,845,628 B2 | 9/2014 | Babkin et al. | |
| 8,888,768 B2 | 11/2014 | Babkin et al. | |
| 8,945,106 B2 | 2/2015 | Arless et al. | |
| 9,095,320 B2 | 8/2015 | Littrup et al. | |
| 9,155,476 B2 | 10/2015 | Fojtik | |
| 9,408,656 B2 | 8/2016 | Littrup et al. | |
| 9,480,521 B2 | 11/2016 | Kim et al. | |
| 10,159,521 B2 | 12/2018 | Jannicke et al. | |
| 10,182,742 B2 | 1/2019 | Condie et al. | |
| 10,194,978 B2 | 2/2019 | Coulombe | |
| 10,271,899 B2 | 4/2019 | Deac | |
| 10,405,919 B2 | 9/2019 | Fung et al. | |
| 10,575,156 B2 | 2/2020 | Shedletsky et al. | |
| 10,667,854 B2 | 6/2020 | Babkin et al. | |
| 11,179,186 B2 * | 11/2021 | Babkin | A61B 18/02 |
| 11,883,085 B2 * | 1/2024 | Babkin | A61B 18/02 |
| 2001/0024485 A1 | 9/2001 | Rogers | |
| 2001/0037812 A1 | 11/2001 | Dobak, III et al. | |
| 2001/0047134 A1 | 11/2001 | Holdaway et al. | |
| 2002/0007180 A1 | 1/2002 | Wittenberger et al. | |
| 2002/0049409 A1 | 4/2002 | Noda et al. | |
| 2002/0062831 A1 | 5/2002 | Beyar et al. | |
| 2002/0072741 A1 | 6/2002 | Sliwa et al. | |
| 2002/0087152 A1 | 7/2002 | Mikus et al. | |
| 2002/0151331 A1 | 10/2002 | Abdelmonem et al. | |
| 2003/0040740 A1 | 2/2003 | Kovalcheck et al. | |
| 2003/0055415 A1 | 3/2003 | Yu et al. | |
| 2003/0065371 A1 | 4/2003 | Satake | |
| 2003/0088240 A1 | 5/2003 | Saadat | |
| 2003/0195605 A1 | 10/2003 | Kovalcheck et al. | |
| 2003/0199817 A1 | 10/2003 | Thompson et al. | |

| | | | |
|---|---|---|---|
| 2004/0027462 A1 | 2/2004 | Hing | |
| 2004/0044334 A1 | 3/2004 | LaFontaine | |
| 2004/0082943 A1 | 4/2004 | Littrup et al. | |
| 2004/0118144 A1 | 6/2004 | Hsu et al. | |
| 2004/0148004 A1 | 7/2004 | Wallsten | |
| 2004/0215294 A1 | 10/2004 | Littrup et al. | |
| 2004/0215295 A1 | 10/2004 | Littrup et al. | |
| 2005/0027247 A1 | 2/2005 | Carrison et al. | |
| 2005/0027289 A1 | 2/2005 | Castellano et al. | |
| 2005/0049345 A1 | 3/2005 | Greiner et al. | |
| 2005/0101903 A1 | 5/2005 | Kohler et al. | |
| 2005/0209587 A1 | 9/2005 | Joye et al. | |
| 2005/0261573 A1 | 11/2005 | Satoh et al. | |
| 2005/0261753 A1 | 11/2005 | Littrup et al. | |
| 2005/0273090 A1 | 12/2005 | Nieman et al. | |
| 2006/0212028 A1 | 9/2006 | Joye et al. | |
| 2006/0235357 A1 | 10/2006 | Woodward et al. | |
| 2006/0235375 A1 | 10/2006 | Littrup et al. | |
| 2006/0247611 A1 | 11/2006 | Abboud et al. | |
| 2006/0253114 A1 | 11/2006 | Saadat | |
| 2008/0119836 A1 | 5/2008 | Littrup et al. | |
| 2008/0312644 A1 | 12/2008 | Fourkas et al. | |
| 2009/0118723 A1 | 5/2009 | Lalonde et al. | |
| 2010/0057063 A1 | 3/2010 | Arless et al. | |
| 2010/0179524 A1 | 7/2010 | Whayne et al. | |
| 2010/0198040 A1 * | 8/2010 | Friedman | A61B 18/1492 606/41 |
| 2010/0256621 A1 | 10/2010 | Babkin et al. | |
| 2011/0009854 A1 | 1/2011 | Babkin et al. | |
| 2011/0028960 A1 | 2/2011 | Tin | |
| 2011/0029048 A1 | 2/2011 | Mahrouche | |
| 2011/0040297 A1 | 2/2011 | Babkin et al. | |
| 2011/0054453 A1 | 3/2011 | Lalonde | |
| 2011/0087070 A1 | 4/2011 | Tilson et al. | |
| 2011/0125143 A1 | 5/2011 | Gross et al. | |
| 2011/0162390 A1 | 7/2011 | Littrup et al. | |
| 2011/0184399 A1 | 7/2011 | Wittenberger | |
| 2011/0282250 A1 * | 11/2011 | Fung | A61B 18/1492 606/1 |
| 2011/0313410 A1 * | 12/2011 | Werneth | A61B 18/02 607/104 |
| 2012/0059364 A1 * | 3/2012 | Baust | A61B 18/02 606/14 |
| 2012/0109118 A1 | 5/2012 | Lalonde et al. | |
| 2012/0143131 A1 | 6/2012 | Tun et al. | |
| 2012/0184955 A1 | 7/2012 | Pivotto et al. | |
| 2012/0253336 A1 | 10/2012 | Littrup et al. | |
| 2013/0073014 A1 | 3/2013 | Lim et al. | |
| 2013/0197498 A1 | 8/2013 | Laske et al. | |
| 2013/0204241 A1 | 8/2013 | Baust | |
| 2013/0218150 A1 | 8/2013 | Amann et al. | |
| 2013/0324987 A1 | 12/2013 | Leung et al. | |
| 2013/0331829 A1 | 12/2013 | Babkin et al. | |
| 2013/0345688 A1 | 12/2013 | Babkin et al. | |
| 2014/0012244 A1 | 1/2014 | Burnett et al. | |
| 2014/0031804 A1 | 1/2014 | Lalonde | |
| 2014/0364848 A1 | 12/2014 | Heimbecher et al. | |
| 2015/0018809 A1 | 1/2015 | Mihalik | |
| 2015/0112328 A1 | 4/2015 | Willard et al. | |
| 2015/0250524 A1 | 9/2015 | Moriarty et al. | |
| 2016/0135864 A1 | 5/2016 | Babkin | |
| 2016/0220294 A1 | 8/2016 | Babkin et al. | |
| 2016/0227600 A1 | 8/2016 | Shedletsky et al. | |
| 2016/0249859 A1 | 9/2016 | Babkin et al. | |
| 2016/0249970 A1 | 9/2016 | Yu et al. | |
| 2017/0049495 A1 | 2/2017 | Yu et al. | |
| 2017/0151008 A1 | 6/2017 | Mazor et al. | |
| 2018/0303535 A1 | 10/2018 | Yu et al. | |
| 2019/0038171 A1 | 2/2019 | Howard | |
| 2019/0076179 A1 | 3/2019 | Babkin et al. | |
| 2019/0125422 A1 | 5/2019 | Babkin et al. | |
| 2019/0209229 A1 | 7/2019 | Babkin et al. | |
| 2019/0254735 A1 | 8/2019 | Stewart et al. | |
| 2019/0262056 A1 | 8/2019 | Yang et al. | |

(56) References Cited

U.S. PATENT DOCUMENTS

| | | | |
|---|---|---|---|
| 2019/0357959 A1 | 11/2019 | Hou et al. | |
| 2020/0261136 A1 | 8/2020 | Babkin et al. | |

FOREIGN PATENT DOCUMENTS

| | | |
|---|---|---|
| JP | H07136180 A | 5/1995 |
| JP | 2008515469 A | 5/2008 |
| WO | 9308751 A1 | 5/1993 |
| WO | 1993008751 A1 | 5/1993 |
| WO | 9749344 A1 | 12/1997 |
| WO | 1997049344 A1 | 12/1997 |
| WO | 0211638 A1 | 2/2002 |
| WO | 2002058576 A1 | 8/2002 |
| WO | 2002096270 A2 | 12/2002 |
| WO | 2002011638 A9 | 4/2003 |
| WO | 2004064914 A2 | 3/2005 |
| WO | 2006137887 A2 | 12/2006 |
| WO | 2009009398 A1 | 1/2009 |
| WO | 2009067497 A1 | 5/2009 |
| WO | 2013007831 A1 | 1/2013 |
| WO | 2013013098 A1 | 1/2013 |
| WO | 2013013099 A1 | 1/2013 |
| WO | 2015047961 A2 | 4/2015 |
| WO | 2015057450 A1 | 4/2015 |
| WO | 2015160574 A1 | 10/2015 |
| WO | 2016123390 A1 | 8/2016 |
| WO | 2017048965 A1 | 3/2017 |
| WO | 2017095756 A1 | 6/2017 |

OTHER PUBLICATIONS

Australian Examination Report No. 1, dated Jul. 31, 2018 for 2014327045.

Barron, Randall F., "Cryogenic Heat Transfer," pp. 97, 129 and 130, Taylor & Francis, 1999.

Bunch TJ, Cutler MJ, Is pulmonary vein isolation still the cornerstone in atrial fibrillation ablation? J Thorac Dis. Feb. 2015;7(2):132-41.a.

Callans DJ, Gerstenfeld EP, Dixit S, et al. Efficacy of repeat pulmonary vein isolation procedures in patients with recurrent atrial fibrillation. J Cardiovasc Electrophysiol 2004; 15:1050-5.

European Search Report for EP04702597 dated Sep. 18, 2007.

European Search Report for EP05858178.6 dated Nov. 5, 2010.

European Search Report for EP08852254 dated Nov. 19, 2010.

European Search Report for EP10184565 dated Feb. 21, 2011.

European Search Report for EP16803999 dated Jan. 7, 2019.

International Preliminary Examination Report dated Oct. 18, 2016 for PCT/US2015/24778.

International Preliminary Examination Report dated Mar. 19, 2020 for PCT/US2018/049467.

International Search Report /Written Opinion dated Jan. 14, 2009 for PCT/US2008/84004.

International Search Report dated Mar. 18, 2015 of PCT/US2014/056839.

International Search Report dated Apr. 25, 2019 of PCT/US2019/012754.

International Search Report dated May 24, 2019 of PCT/US2019/012789.

International Search Report dated Nov. 21, 2018 of PCT/US2018/049467.

International Search Report dated Dec. 28, 2016 of the counterpart application PCT/US16/33833.

International Search Report dated Oct. 1, 2012 for PCT/US2012/47487.

International Search Report dated Jan. 21, 2015 for PCT/US2014/59684.

International Search Report dated Jul. 8, 2015 for PCT/US2015/24778.

International Search Report dated Jan. 15, 2016 for PCT/US2015/56780.

International Search Report dated Jan. 31, 2017 for PCT/US2016/51954.

International Search Report dated Feb. 2, 2017 for PCT/US2016/63882.

Kim et al. Linear ablation in addition to circumferential pulmonary vein isolation (Dallas lesion set) does not improve clinical outcome in patients with paroxysmal atrial fibrillation: a prospective randomized study. Europace. Mar. 2015;17(3):388-95.

Kowalski M, Grimes MM, Perez FJ, et al. Histopathologic characterization of chronic radiofrequency ablation lesions for pulmonary vein isolation. J Am Coll Cardiol 2012;59:930-8.

Lemola, Kristina, MD, et al., "Pulmonary Vein Isolation as an End Point for Left Atrial Circumferential Ablation of Atrial Fibrillation," Journal of American College of Cardiology, vol. 46, No. 6, 2005.

Lide, D.R. and Keihiaian, H.V., "CRC Handbook of Thermophysical and Thermochemical Data," p. 375, CRC Press 1994.

McGann CJ, Kholmovski EG, Oakes RS, et al. New magnetic resonance imaging-based method for defining the extent of left atrial wall injury after the ablation of atrial fibrillation. J Am Coll Cardiol 2008;52:1263-71.

Ouyang F, Tilz R, Chun J, et al. Long-term results of catheter ablation in paroxysmal atrial fibrillation: lessons from a 5-year follow-up. Circulation 2010;122:2368-77.

Ranjan R, Kato R, Zviman MM, et al. Gaps in the ablation line as a potential cause of recovery from electrical isolation and their visualization using MRI. Circ Arrhythm Electrophysiol 2011;4:279-86.

Rolf, Sascha, MD, et al., "Electroanatomical Mapping of Atrial Fibrillation: Review of the Current Techniques and Advances," Journal of Artrial Fibrillation, vol. 7, Issue 4, Dec. 2014-Jan. 2015.

Sawhney N, Anousheh R, Chen WC, et al. Five-year outcomes after segmental pulmonary vein isolation for paroxysmal atrial fibrillation. Am J Cardiol 2009;104:366-72.

Skanes, Allan C., et al., "Cryoblation: Potentials and Pitfalls," doi: 10.1046/j.1540-8167.2004.15106.x, Jul. 6, 2004.

Stuehlinger, M., et al., "CoolLoop First: A First in Man Study to Test a Novel Circular Cryoablation System in Paroxysmal Artial Fibrillation," Journal of Artial Fibrillation, vol. 81, Issue 3, Oct.-Nov. 2015.

Sun, Ya-ping, Supercritical Fluid Technology in Materials Science and Engineering, pp. 1 and 26, CRC Press 2002.

Supplemental European Search Report dated Apr. 23, 2018 for EP15858716.

Supplementary European Search Report dated Jan. 7, 2019 of the counterpart application EP16803999.8.

Thakore, S.B. and Bhatt, B.I., "Introduction to Process Engineering and Design," Chemical Engineering Series, pp. 27-28, McGraw-Hill 2008.

Verma A, Kilicaslan F, Pisano E, et al. Response of atrial fibrillation to pulmonary vein antrum isolation is directly related to resumption and delay of pulmonary vein conduction. Circulation 2005;112:627-35.

* cited by examiner

950

ENDOVASCULAR NEAR CRITICAL FLUID BASED CRYOABLATION CATHETER AND RELATED METHODS

BACKGROUND

Field

This disclosure relates to cryosurgery and more particularly to cryoablation catheters comprising a fluid operating near its critical point.

Description of the Related Art

Atrial fibrillation is a heart condition in which the left or right atrium of the heart does not beat properly. It is often caused by aberrant electrical behavior of some portion of the atrial wall. Certain parts of the atria, or nearby structures such as the pulmonary veins, can misfire in their production or conduction of the electrical signals that control contraction of the heart, creating abnormal electrical signals that prompt the atria to contract between normal contractions caused by the normal cascade of electrical impulses. This can be caused by spots of ischemic tissue, referred to as ectopic foci, or by electrically active fibers in the pulmonary veins, for example. Currently, the Cox Maze procedure, developed by Dr. James Cox in the 1980's, is a surest method of eliminating atrial fibrillation. In the Cox Maze procedure, the atrial wall is cut with a scalpel in particular patterns which isolate the foci of arrhythmia from the rest of the atrial wall, and then sewn back together. Upon healing, the resultant scar tissue serves to interrupt ectopic re-entry pathways and other aberrant electrical conduction and prevent arrhythmia and fibrillation. There are several variations of the Cox maze procedure, each involving variations in the number and placement of lesions created.

The original Cox maze procedure was an open chest procedure requiring surgically opening the atrium after opening the chest. The procedure itself has a high success rate, though due to the open chest/open heart nature of the procedure, and the requirement to stop the heart and establish a coronary bypass, it is reserved for severe cases of atrial fibrillation.

The Cox maze procedure has been performed using ablation catheters in both transthoracic epicardial approaches and transvascular endocardial approaches. In transthoracic epicardial approaches, catheters or small probes are used to create linear lesions in the heart wall along lines corresponding to the maze of the Cox maze procedure. In the transvascular endocardial approaches, a catheter is navigated through the vasculature of the patient to the atrium, pressed against the inner wall of the atrium, and energized to create lesions corresponding to the maze of the Cox maze procedure.

In either approach, various ablation catheters have been proposed for creation of the lesion, including flexible cryoprobes or cryocatheters, bipolar RF catheters, monopolar RF catheters (using ground patches on the patient's skin), microwave catheters, laser catheters, and ultrasound catheters. These approaches are attractive because they are minimally invasive and can be performed on a beating heart. However, these approaches have a low success rate. The low success rate may be due to incomplete lesion formation. A fully transmural lesion is required to ensure that the electrical impulse causing atrial fibrillation are completely isolated from the remainder of the atrium, and this is difficult to achieve with beating heart procedures.

A major challenge to the effective epicardial application of ablative energy sources to cardiac tissue without the use of the heart-lung machine ("off-pump") is that during normal heart function the atria are filled with blood at 37° C. that is moving through the atria at roughly 5 liters per minute. If cryothermia energy is applied epicardially, this atrial blood flow acts as a "cooling sink," warming the heart wall and making it difficult to lower the endocardial surface of the atrial wall to a lethal temperature (roughly −30° C.). Thus, lesion transmurality is extremely difficult to attain.

Similarly, if heat-based energy sources such as RF, microwave, laser, or HIFU are applied to the epicardial surface without using the heart-lung machine to empty the atria, the blood flowing through the atrium acts as a heat sink, cooling the heart wall making it difficult to raise the endocardial surface of the atrial wall to a lethal temperature (roughly 55° C.).

Another shortcoming with certain cryosurgical apparatus arises from evaporation. The process of evaporation of a liquefied gas results in enormous expansion as the liquid converts to a gas; the volume expansion is on the order of a factor of 200. In a small-diameter system, this degree of expansion consistently results in a phenomenon known in the art as "vapor lock." The phenomenon is exemplified by the flow of a cryogen in a thin-diameter tube, such as is commonly provided in a cryoprobe. A relatively massive volume of expanding gas that forms ahead of it impedes the flow of the liquid cryogen.

Traditional techniques that have been used to avoid vapor lock have included restrictions on the diameter of the tube, requiring that it be sufficiently large to accommodate the evaporative effects that lead to vapor lock. Other complex cryoprobe and tubing configurations have been used to "vent" $N_2$ gas as it formed along transport tubing. These designs also contributed to limiting the cost efficacy and probe diameter.

There is accordingly a need for improved methods and systems for providing minimally invasive, safe and efficient cryogenic cooling of tissues.

SUMMARY

The description, objects and advantages of the present disclosure will become apparent from the detailed description to follow, together with the accompanying drawings.

An endovascular near critical fluid based cryoablation catheter for creating an elongated lengthwise-continuous lesion in tissue comprises an elongated shaft; a flexible distal tissue treatment section; and a distal tip. At least one fluid delivery tube extends through the distal treatment section to transport a near critical fluid towards the distal tip. At least one fluid return tube extends through the distal treatment section to transport the near critical fluid away from the distal tip. The distal treatment section also includes a flexible fluid-sealed cover or barrier layer surrounding the delivery tubes. The cover and tubes collectively define a space which is filled with a fluidic thermally conductive media. The thermally conductive media, fluid delivery tubes, and the cover are arranged such that a flow of the near critical fluid through the tube bundle transfers heat between a target tissue and the distal treatment section of the catheter thereby creating the elongated lengthwise-continuous lesion in the tissue.

In embodiments, the distal treatment section is deflected along a contour of the endocardium surface and has cooling power to create the elongate continuous lesion transmurally.

In embodiments, an endovascular near critical based flexible multi-tubular cryoprobe includes a housing for receiving an inlet flow of cryogenic fluid from a fluid source and for discharging an outlet flow of the cryogenic fluid. A plurality of fluid transfer tubes are securely attached to the housing. This includes a set of inlet fluid transfer tubes for receiving the inlet flow from the housing; and, a set of outlet fluid transfer tubes for discharging the outlet flow to the housing. Each of the fluid transfer tubes is formed of material that maintains flexibility in a full range of temperatures from −200° C. to ambient temperature. Each fluid transfer tube has an inside diameter in a range of between about 0.10 mm and 1.0 mm and a wall thickness in a range of between about 0.01 mm and 0.30 mm. An end cap is positioned at the ends of the plurality of fluid transfer tubes to provide fluid transfer from the inlet fluid transfer tubes to the outlet fluid transfer tubes. In embodiments, the plurality of fluid transfer tubes are encapsulated with a cover and thermally conductive media.

In embodiments, an endovascular near critical Nitrogen based cryoablation system for creating an elongate lengthwise-continuous lesion in tissue comprises a near critical Nitrogen pressure generator; a near critical Nitrogen cooler for cooling the near critical Nitrogen; a near critical Nitrogen based endovascular cryoablation catheter in fluid communication with the generator; and a controller operable to control the cooling power delivered from a distal treatment section of the catheter to the tissue to create the elongate lengthwise-continuous lesion. The distal treatment section has a shape effective to create a continuous linear-shaped lesion along an interior wall of the heart and wherein the lesion has a length ranging from 2 to 10 cm., and extends through the entire wall of the heart for the entire length of the lesion. In embodiments, the system further comprises a timer to signal when to stop delivering cooling power.

In embodiments, a method for treating atrial fibrillation includes a) inserting a cryoablation catheter comprising a distal treatment section into a patient's vasculature; b) navigating the distal treatment section to the heart, and through an opening in the heart until the distal treatment section is within a space in the heart; c) manipulating the distal treatment section of the catheter against a linearly disposed target section of cardiac tissue along an interior wall of the heart; d) creating the elongate lengthwise-continuous lesion by circulating a near critical fluid through at least one fluid delivery tube and at least one fluid return tube extending through the distal treatment section while protecting for leaks with a protective cover and a thermally conductive media in the space between the cover and the tubes. In embodiments, the step of creating is halted after a threshold condition is established. In embodiments, the step of inserting the cryoablation catheter is carried out by inserting the cryoablation catheter through a guide catheter.

In embodiments, an endovascular near critical fluid based cryoablation catheter for creating an elongated lengthwise-continuous lesion in tissue comprises an elongated shaft; a flexible distal tissue treatment section; a distal tip; a plurality of fluid delivery tubes extending through the distal treatment section to transport the near critical fluid towards the distal tip. Each of the fluid delivery tubes is surrounded by a flexible fluid-sealed cover. A space between the cover and the fluid delivery tube is filled with a thermally conductive media.

In embodiments the catheter additionally includes a plurality of fluid return tubes extending through the distal treatment section to transport the near critical fluid away from the distal tip. Each of the fluid return tubes is surrounded by the flexible fluid-sealed cover. A gap between the cover and the fluid return tube is filled with the thermally conductive media. A flow of a near critical fluid is transported through the fluid delivery tubes and fluid return tubes and transfers heat between a target tissue and the distal treatment section of said catheter thereby creating the elongated lengthwise-continuous lesion in the tissue.

DETAILED DESCRIPTION

Figure 1A:
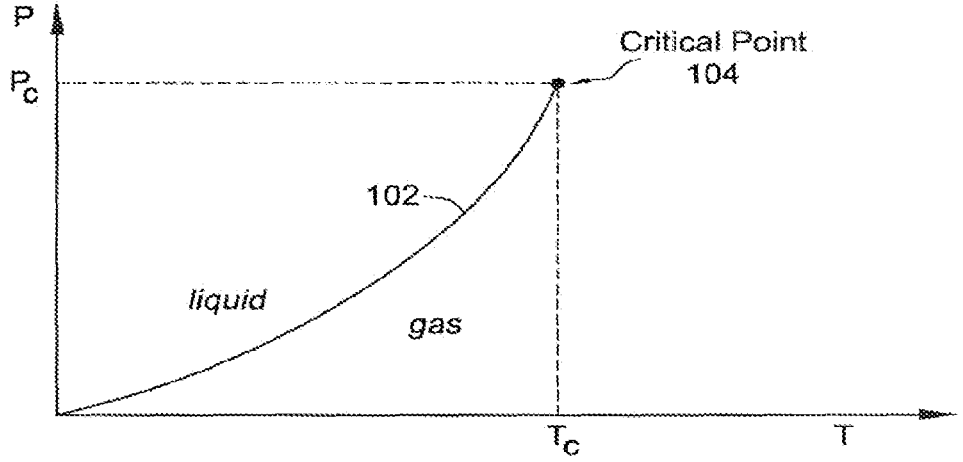
FIG. 1A illustrates a typical cryogen phase diagram.

Before the present disclosure is described in detail, it is to be understood that this disclosure is not limited to particular variations set forth herein as various changes or modifications may be made to the disclosure described and equivalents may be substituted without departing from the spirit and scope of the disclosure. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. In addition, many modifications may be made to adapt a particular situation, material, composition of matter, process, process act(s) or step(s) to the objective(s), spirit or scope of the present disclosure. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the disclosure. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail). The referenced items are provided solely for their disclosure prior to the filing date of the present application.

Nothing herein is to be construed as an admission that the present disclosure is not entitled to antedate such material by virtue of prior disclosure.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Embodiments of the disclosure make use of thermodynamic processes using cryogens that provide cooling without encountering the phenomenon of vapor lock.

Malleable and flexible cryoprobes are described in U.S. Pat. No. 6,161,543, hereby incorporated by reference in its entirety, issued to Cox et al. The described probe has a malleable shaft. A malleable metal rod is coextruded with a polymer to form the shaft. The rod permits the user to shape the shaft as necessary so that a tip can reach the tissue to be ablated.

U.S. Pat. No. 5,108,390, hereby incorporated by reference in its entirety, issued to Potocky et al, discloses a highly flexible cryoprobe that can be passed through a blood vessel and into the heart without external guidance other than the blood vessel itself.

Several patents disclose the use of bellows-type assemblies for use with cryoablation systems. For example, U.S. Pat. No. 6,241,722, hereby incorporated by reference in its entirety, issued to Dobak et al, discloses a cryogenic catheter with a bellows and which utilizes a longitudinally movable Joule-Thomson nozzle of expansion. The Dobak '722 device preferably uses closed media-flow pathways for recycling of the media employed.

Dobak et al, in U.S. Pat. No. 5,957,963, hereby incorporated by reference in its entirety, discloses the use of a flexible catheter inserted through the vascular system of a patient to place the distal tip of the catheter in an artery feeding a selected organ of the patient. The '963 patent discloses a heat transfer bellows for cooling the blood flowing through the artery.

U.S. Pat. No. 6,767,346, hereby incorporated by reference in its entirety, issued to Damasco et al, entitled, "Cryosurgical Probe With Bellows Shaft", discloses use of a cryosurgical probe with a bellows shaft. U.S. Pat. No. 6,936,045, hereby incorporated by reference in its entirety, issued to Yu et al, entitled, "Malleable Cryosurgical Probe" discloses a cryosurgical probe used for Joule-Thomson nozzles.

CryoCath Technologies, Inc., Montreal, Quebec, Canada, utilizes a cryoablation probe trademarked under the name SURGIFROST® which involves the use of a cryoprobe with a malleable or corrugated shell.

A problem with this and other similar products, however, is that these cryoprobes are not sufficiently flexible for optimum use and still retain memory. As a result, there is often an incomplete/intermittent thermal contact along the whole line of freezing. The small contact area provides a limitation for the power delivered to the tissue.

Additionally, there are substantial limits on flexibility and conformability of the treatment regions of the cryoablation apparatus. If the distal treatment section is too delicate and a breach in the cover occurs, cryogen may leak into the bloodstream. Substantial danger may result, perhaps death. Bubbles and/or cryogen in the heart, for example, may be immediately sent to the vessels in the brain. Such circumstances may result in highly undesirable neuro-ischemic events.

Various others have attempted to reduce the likelihood of a cryogenic fluid leaking into the bloodstream. U.S. Pat. No. 7,648,497 to Lane, hereby incorporated by reference in its entirety, for example, provides a second balloon surrounding a first balloon. The space between the first balloon and the second balloon is under vacuum. However, use of vacuum is undesirable because it is a very weak thermal conductor. Use of a weak thermal conductor reduces cooling power.
Cryogen Phase Diagram and Near Critical Point This application uses phase diagrams to illustrate and compare various thermodynamic processes. An example phase diagram is shown in FIG. 1A. The axes of the diagram correspond to pressure P and temperature T, and includes a phase line 102 that delineates the locus of all (P, T) points where liquid and gas coexist. For (P, T) values to the left of the phase line 102, the cryogen is in a liquid state, generally achieved with higher pressures and lower temperatures, while (P, T) values to the right of the phase line 102 define regions where the cryogen is in a gaseous state, generally achieved with lower pressures and higher temperatures. The phase line 102 ends abruptly in a single point known as the critical point 104. In the case of nitrogen $N_2$, the critical point is at $P_c=33.94$ bar and $T_c=-147.15°$ C.

When a fluid has both liquid and gas phases present during a gradual increase in pressure, the system moves up along the liquid-gas phase line 102. In the case of $N_2$, the liquid at low pressures is up to two hundred times more dense than the gas phase. A continual increase in pressure causes the density of the liquid to decrease and the density of the gas phase to increase, until they are exactly equal only at the critical point 104. The distinction between liquid and gas disappears at the critical point 104. The blockage of forward flow by gas expanding ahead of the liquid cryogen can thus be avoided by conditions surrounding the critical point, defined herein as "near-critical conditions." Factors that allow greater departure from the critical point while maintaining a functional flow include greater speed of cryogen flow, larger diameter of the flow lumen and lower heat load upon the thermal exchanger, or cryoprobe tip.

As the critical point is approached from below, the vapor phase density increases and the liquid phase density decreases until right at the critical point, where the densities of these two phases are exactly equal. Above the critical point, the distinction of liquid and vapor phases vanishes, leaving only a single, supercritical phase. All gases obey quite well the following van der Waals equation of state:

$$(p+3/v^2)(3v-1)=8t \qquad \text{[Eq. 1]}$$

where $p=P/P_c$, $v=V/V_c$, and $t=T/T_c$, and $P_c$, $V_c$, and $T_c$ are the critical pressure, critical molar volume, and the critical temperature respectively.

The variables v, p, and t are often referred to as the "reduced molar volume," the "reduced pressure," and the "reduced temperature," respectively. Hence, any two substances with the same values of p, v, and t are in the same thermodynamic state of fluid near its critical point. Eq. 1 is thus referred to as embodying the "Law of Corresponding States." This is described more fully in H. E. Stanley, *Introduction to Phase Transitions and Critical Phenomena* (Oxford Science Publications, 1971), the entire disclosure of which is incorporated herein by reference for all purposes. Rearranging Eq. 1 provides the following expression for v as a function of p and t:

$$pv^3-(p+8t)v^2+9v-3=0. \qquad \text{[Eq. 2]}$$

The reduced molar volume of the fluid v may thus be thought of as being an exact function of only the reduced pressure t and the reduced pressure p.

Typically, in embodiments of the disclosure, the reduced pressure p is fixed at a constant value of approximately one, and hence at a fixed physical pressure near the critical pressure, while the reduced temperature t varies with the heat load applied to the needle. If the reduced pressure p is a constant set by the engineering of the system, then the reduced molar volume v is an exact function of the reduced temperature t. In embodiments of the disclosure, the needle's operating pressure p may be adjusted so that over the course of variations in the temperature t of the needle, v is maintained below some maximum value at which the vapor lock condition will result. It is generally advantageous to maintain p at the lowest value at which this is true since boosting the pressure to achieve higher values of p may involve use of a more complex and more expensive compressor, resulting in more expensive procurement and maintenance of the entire needle support system and lower overall wall plug efficiency. As used herein, "wall plug efficiency" refers to the total cooling power of the apparatus divided by the power obtained from a line to operate the system.

The conditions that can be placed on v depend in a complex and non-analytic way on the volume flow rate dV/dt, the heat capacity of the liquid and vapor phases, and the transport properties such as the thermal conductivity, viscosity, etc., in both the liquid and the vapor. This exact relationship cannot be derived in closed form algebraically, but may be determined numerically by integrating the model equations that describe mass and heat transport within the needle. Conceptually, vapor lock occurs when the rate of heating of the needle produces the vapor phase, and when the cooling power of this vapor phase, which is proportional to the flow rate of the vapor times its heat capacity divided by its molar volume, is not able to keep up with the rate of heating to the needle. When this occurs, more and more of the vapor phase is formed in order to absorb the excess heat through the conversion of the liquid phase to vapor in the cryogen flow. This creates a runaway condition where the liquid converts into vapor phase to fill the needle, and effectively all cryogen flow stops due to the large pressure that results in this vapor phase as the heat flow into the needle increases its temperature and pressure rapidly. This condition is called "vapor lock." Since the liquid and vapor phases are identical in their molar volume, and hence cooling power at the critical point, the cooling system at or above the critical point can never vapor lock. But for conditions slightly below the critical below the critical point, the needle may avoid vapor lock as well. A relationship between a minimum acceptable molar volume, corresponding to the minimum acceptable gas phase density, and dimensions of the needle, flow rate, and thermophysical properties of gas and liquid phases is a consequence of a manifestly complex nonlinear system. A determination of how large v may be, and hence how small p may be, to reliably avoid vapor lock may be determined experimentally, as illustrated with the data shown in FIG. 1B.

Figure 1B:
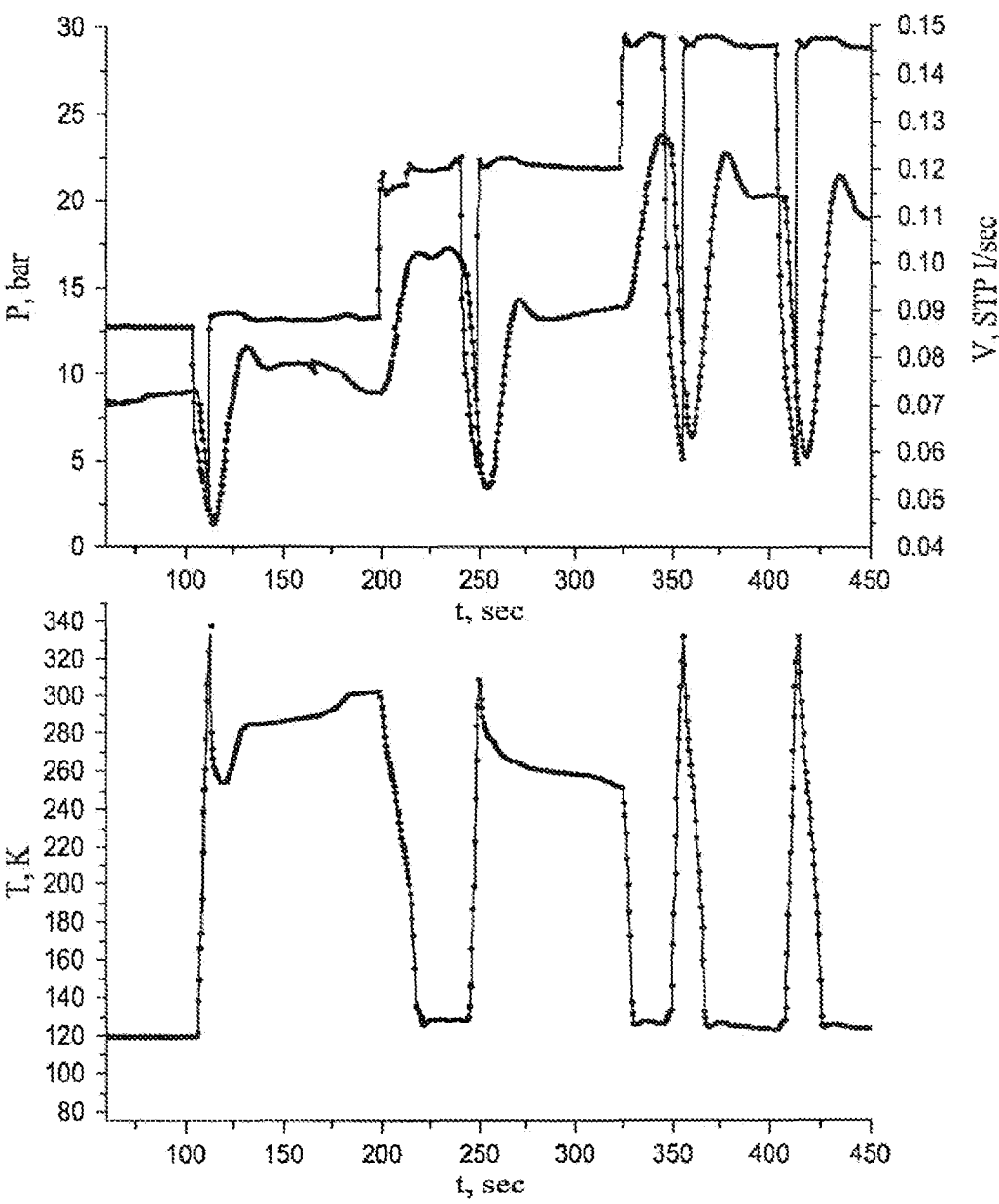
FIG. 1B provides an illustration of an embodiment of how to determine a minimum operating pressure for a cryogenic probe.

FIG. 1B displays how a minimum operating pressure P, and hence the minimum reduced pressure p, is determined experimentally. The upper curve in the top panel shows the pressure of nitrogen in the needle and the bottom curve in the top panel shows the resulting mass flow rate through the probe, displayed in units of standard liters per second through the needle. The bottom panel shows the needle tip temperature at the same times as the top plot. A heat load of 6.6 W was applied to the needle tip while these data were taken. For example, at an operating pressure of 12.6 bar and 22 bar a vapor-lock condition occurred at this level of heat load and flow rate, as evidenced by the failure of the needle tip temperature to recover its low temperature value when the flow was momentarily interrupted and then resumed. But at 28.5 bar of pressure, the tip temperature recovered its low temperature value reliably following a flow interruption. The downwards trend in the mass flow rate through the needle is indicative of being very close, yet slightly below the lowest acceptable pressure for reliable, continuous operation without vapor lock. These data suggest that about 29 bars of pressure may be the lowest acceptable operating pressure in this illustrative embodiment. Thus, for this embodiment, in which a vacuum jacketed needle with 22-cm long capillaries of 0.020-cm diameter for the inflow capillary and 0.030-cm diameter for the outflow capillary, under this heat load and flow rate, 29 bar is a typical minimum operating pressure. This corresponds to a minimum operating pressure to avoid vapor lock of about 85% or more of the critical pressure.

Figure 1C:
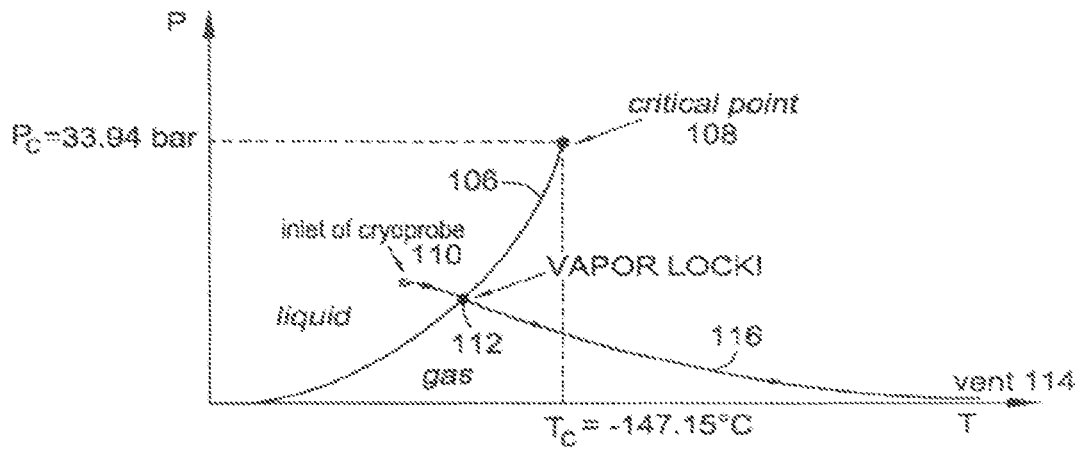
FIG. 1C uses a cryogen phase diagram to illustrate the occurrence of vapor lock with simple-flow cryogen cooling.

The occurrence of vapor lock in a simple-flow cryogen cooling system may be understood with reference to FIG. 1C, which for exemplary purposes shows the phase diagram for $N_2$, with liquid-gas phase line 106 terminating at critical point 108. The simple-flow cooling proceeds by compressing the liquid cryogen and forcing it to flow through a cryoprobe. Some pre-cooling may be used to force liquid-phase cryogen through an inlet 110 of the cryoprobe from the indicated point on the phase diagram to the region where the cryogen evaporates to provide evaporative cooling. The thermodynamic path 116 taken by the cryogen as it is forced from the inlet 110 to a vent 114 intersects the liquid-gas phase line 106 at point 112, where the evaporation occurs. Because the evaporation occurs at a point along the liquid-gas phase line 106 well below the critical point 108, there is a dramatic expansion of the volume of the flow stream as the much denser liquid evaporates into its gaseous phase, leading to the occurrence of vapor lock.

Joule-Thomson Cooling

An alternative cryogen cooling technique that avoids vapor lock at the expense of a number of complexities exploits the Joule-Thomson effect. When a gas is compressed, there is a reduction in its enthalpy, the size of the reduction varying with the pressure. When the gas is then expanded through a small port (referred to as a "JT port" or "throttle") to a lower pressure, there is a reduction in temperature, with the resultant cooling being a function of the decrease in enthalpy during compression. With a heat exchanger provided between the compressor and expansion valve, progressively lower temperatures may be reached. In some instances, Joule-Thomson cooling uses cheaper gases like $CO_2$ or $N_2O$, although lower temperatures can be achieved with argon (Ar). There may be higher risks associated with Ar in addition to its higher cost, but both of these may be justified in some applications because of the rapid initiation and termination of freezing that may be provided.

Figure 7:
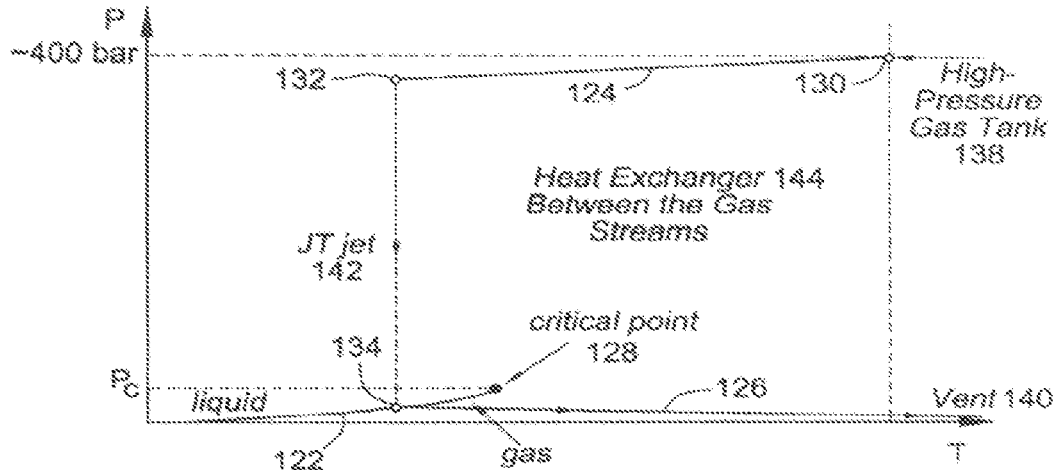
FIG. 7 uses a cryogen phase diagram to illustrate a cooling cycle used in Joule-Thomson cooling to avoid the occurrence of vapor lock.

Joule-Thomson cooling processes thus use a completely different cooling cycle than is used for simple-flow cryogen cooling, as illustrated with the phase diagram of FIG. 7. The cooling cycle is shown superimposed on the $N_2$ phase diagram as a specific example, with the liquid-gas phase line 122 for $N_2$ terminating at its critical point 128. Nitrogen is initially provided at very high pressures at normal ambient (room) temperature at point 130 on the phase diagram. The pressure is typically about 400 bar, i.e. greater than ten times the pressure at the critical point 128. The $N_2$ flows within a cryoprobe along thermodynamic path 124 until it reaches the JT expansion port at point 132 on the phase diagram. The $N_2$ expands abruptly at the JT port, flowing in a JT jet 142 downwards in the phase diagram as its pressure decreases rapidly. The rapid expansion causes the $N_2$ downstream in the jet 142 to partially liquefy so that following the expansion at the JT jet 142, the liquefied $N_2$ is in thermal equilibrium with its gaseous phase. The nitrogen is thus at point 134 in the phase diagram, i.e. on the liquid-gas phase line 106 slightly above ambient pressure, and therefore well below the critical point 128. The nitrogen is heated on a return gas stream following thermodynamic path 126 where it may be used for cooling, and is subsequently exhausted to ambient conditions through a vent 140, perhaps on the way back to a controlling console. It is notable that Joule-Thomson cooling may never approach the critical point of the liquid-gas system, and that it uses predominantly evaporative-flow cooling.

The flow of the cooled gas in Joule-Thomson cooling is typically provided back along a side of the inlet high-pressure feed line. This counter-flow of the low-pressure return gas advantageously cools the incoming high-pressure gas before expansion. The effect of this heat exchanger 144 between the gas streams is evident in the phase diagram since the pressure along the inlet line to the JT port (thermodynamic path 124) falls due to its flow impedance as the stream of high-pressure gas is cooled by the counter-flow heat exchanger. Similarly, the pressure of the return stream (thermodynamic path 126) falls slightly as the cold, low-pressure nitrogen cools the incoming stream at high pressure through the counter-flow heat exchanger 144. The effects of the counter-flow heat exchanger 144 are beneficial in improving the efficiency the Joule-Thomson cooling, but limits to this efficiency result from trying to make the cryoprobe needle smaller in diameter. As the cryoprobe needle becomes smaller, the return-gas-flow velocity becomes larger, eventually reaching the speed of sound for typical volume flow rates and probe designs in probes having a diameter of about 1.5 mm The Joule-Thomson cooling process continues to lose efficiency as the probe is miniaturized further, to the point where no more cooling power can be generated. Probes with diameters <1.2 mm can be thereby severely limited by the physics of their operation to the point where they would have minimal cooling capacity, even if they could be reliably constructed at a reasonable cost. The cost of Joule-Thomson probe construction increases rapidly as the probe diameter is reduced, primarily because of the fabrication and assembly costs associated with the counter-flow heat exchanger.

Embodiments of the disclosure can avoid the occurrence of vapor lock and permit decreased probe sizes by operating in cryogen pressure-temperature regimes that avoid any crossing of the liquid-gas phase line. In particular embodiments, cryogenic cooling is achieved by operating near the critical point for the cryogen. When operating in this region, heat flows into the near-critical cryogen from the surrounding environment since the critical-point temperature (e.g., $-147°$ C. in the case of $N_2$) is much colder that the surrounding environment. This heat is removed by the flow of the near critical cryogen through the tip of a cryoprobe, even though there is no latent heat of evaporation to assist with the cooling process. While the scope of the disclosure is intended to include operation in any regime having a pressure greater than the critical-point pressure, the cooling efficiency tends to decrease as the pressure is increased above the critical pressure. This is a consequence of increasing energy requirements needed to achieve flow at higher operating pressures.

Cryoablation Systems

Figure 2A:
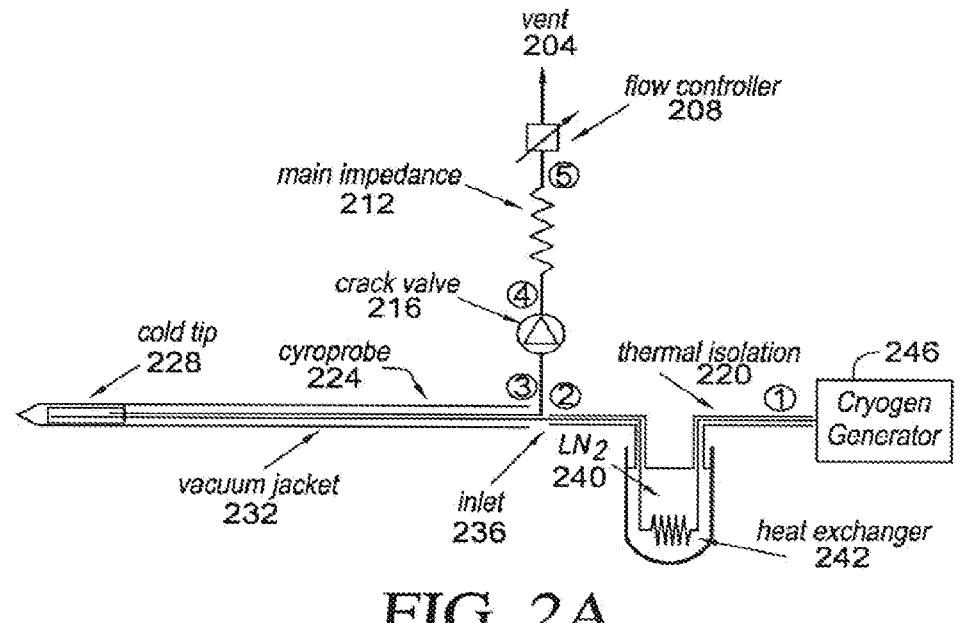
FIG. 2A is a schematic illustration of an embodiment of a cryogenic cooling
system.
Figure 2B:
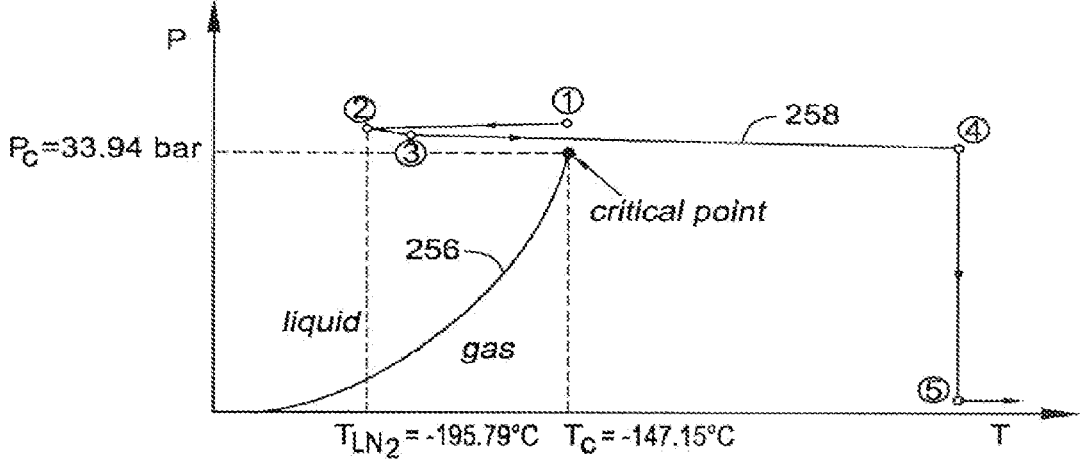
FIG. 2B uses a cryogen phase diagram to illustrate an embodiment of a method for cryogenic cooling.

FIG. 2A provides a schematic illustration of a structural arrangement for a cryogenic system in one embodiment, and FIG. 2B provides a phase diagram that illustrates a thermodynamic path taken by the cryogen when the system of FIG. 2A is operated. The circled numerical identifiers in the two figures correspond so that a physical position is indicated in FIG. 2A where operating points identified along the thermodynamic path are achieved. The following description thus sometimes makes simultaneous reference to both the structural drawing of FIG. 2A and to the phase diagram of FIG. 2B in describing physical and thermodynamic aspects of the cooling flow. For purposes of illustration, both FIGS. 2A and 2B make specific reference to a nitrogen cryogen, but this is not intended to be limiting. The disclosure may more generally be used with any suitable cryogen, as will be understood by those of skill in the art; merely by way of example, alternative cryogens that may be used include argon, helium, hydrogen, and oxygen. In FIG. 2B, the liquid-gas phase line is identified with reference label 256 and the thermodynamic path followed by the cryogen is identified with reference label 258.

A cryogenic generator 246 is used to supply the cryogen at a pressure that exceeds the critical-point pressure $P_c$ for the cryogen at its outlet, referenced in FIGS. 2A and 2B by label {circle around (1)}. The cooling cycle may generally begin at any point in the phase diagram having a pressure above or slightly below $P_c$, although it is advantageous for the pressure to be near the critical-point pressure $P_c$. The cooling efficiency of the process described herein is generally greater when the initial pressure is near the critical-point pressure $P_c$ so that at higher pressures there may be increased energy requirements to achieve the desired flow. Thus, embodiments may sometimes incorporate various higher upper boundary pressure but generally begin near the critical point, such as between 0.8 and 1.2 times $P_c$, and in one embodiment at about 0.85 times $P_c$.

As used herein, the term "near critical" refers to near the liquid-vapor critical point. Use of this term is equivalent to "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient cooling agent. In other words, reference to a near critical point refers to the region where the liquid-vapor system is adequately close to the critical point so that the fluctuations of the liquid and vapor phases are large enough to create a large enhancement of the heat capacity over its background value. The near critical temperature is a temperature within ±10% of the critical point temperature. The near critical pressure is between 0.8 and 1.2 times the critical point pressure.

Referring again to FIG. 2A, the cryogen is flowed through a tube, at least part of which is surrounded by a reservoir 240 of the cryogen in a liquid state, reducing its temperature without substantially changing its pressure. In FIG. 2A, reservoir is shown as liquid $N_2$, with a heat exchanger 242 provided within the reservoir 240 to extract heat from the flowing cryogen. Outside the reservoir 240, thermal insulation 220 may be provided around the tube to prevent unwanted warming of the cryogen as it is flowed from the cryogen generator 246. At point {circle around (2)}, after being cooled by being brought into thermal contact with the liquid cryogen, the cryogen has a lower temperature but is at substantially the initial pressure. In some instances, there may be a pressure change, as is indicated in FIG. 2B in the form of a slight pressure decrease, provided that the pressure does not drop substantially below the critical-point pressure $P_c$, i.e. does not drop below the determined minimum pressure. In the example shown in FIG. 2B, the temperature drop as a result of flowing through the liquid cryogen is about 47° C.

The cryogen is then provided to a device for use in cryogenic applications. In the exemplary embodiment shown in FIG. 2A, the cryogen is provided to an inlet 236 of a cryoprobe 224, such as may be used in medical cryogenic applications, but this is not a requirement.

In embodiments, the cryogen may be introduced through a proximal portion of a catheter, along a flexible intermediate section of the catheter, and into the distal treatment section of the catheter. At the point when the cryogen is provided to such treatment region of the device, indicated by label {circle around (2 and 3)} in FIGS. 2A and 2B, there may be a slight change in pressure and/or temperature of the cryogen as it moves through an interface with the device, i.e. such as when it is provided from the tube to the cryoprobe inlet 236 in FIG. 2A. Such changes may typically show a slight increase in temperature and a slight decrease in pressure. Provided the cryogen pressure remains above the determined minimum pressure (and associated conditions), slight increases in temperature do not significantly affect performance because the cryogen simply moves back towards the critical point without encountering the liquid-gas phase line 256, thereby avoiding vapor lock.

Thermal insulation along the shaft of the cryotherapy apparatus (e.g., needles), and along the support system that delivers near-critical freeze capability to these needles, may use a vacuum of better than one part per million of atmospheric pressure. Such a vacuum may not be achieved by conventional two-stage roughing pumps alone. The percutaneous cryotherapy system in an embodiment thus incorporates a simplified method of absorption pumping rather than using expensive and maintenance-intensive high-vacuum pumps, such as diffusion pumps or turbomolecular pumps. This may be done on an internal system reservoir of charcoal, as well as being built into each individual disposable probe.

Embodiments incorporate a method of absorption pumping in which the liquid nitrogen bath that is used to sub-cool the stream of incoming nitrogen near its critical point is also used to cool a small volume of clean charcoal. The vast surface area of the charcoal permits it to absorb most residual gas atoms, thus lowering the ambient pressure within its volume to well below the vacuum that is used to thermally insulate the needle shaft and the associated support hardware. This volume that contains the cold charcoal is attached through small-diameter tubing to the space that insulates the near-critical cryogen flow to the needles. Depending upon the system design requirements for each clinical use, the charcoal may be incorporated into the cooling reservoir of liquid cryogen 240 seen in FIG. 2A, or become part of the cryoprobe 224, near the connection of the extension hose near the inlet 236. Attachments may be made through a thermal contraction bayonet mount to the vacuum space between the outer shaft of the vacuum jacketed needles and the internal capillaries that carry the near-critical cryogen, and which is thermally insulated from the surrounding tissue. In this manner, the scalability of the system extends from simple design constructions, whereby the charcoal-vacuum concept may be incorporated into smaller reservoirs where it may be more convenient to draw the vacuum. Alternatively, it may be desirable for multiple-probe systems to individually incorporate small charcoal packages into each cryoprobe near the junction of the extension close/cryoprobe with the machine interface 236, such that each hose and cryoprobe draws its own vacuum, thereby further reducing construction costs.

Flow of the cryogen from the cryogen generator 246 through the cryoprobe 224 or other device may be controlled in the illustrated embodiment with an assembly that includes a crack valve 216, a flow impedance, and a flow controller. The cryoprobe 224 itself may comprise a vacuum jacket 232 along its length and may have a cold tip 228 that is used for the cryogenic applications. Unlike a Joule-Thomson probe, where the pressure of the working cryogen changes significantly at the probe tip, these embodiments of the disclosure provide relatively little change in pressure throughout the probe. Thus, at point {circle around (4)}, the temperature of the cryogen has increased approximately to ambient temperature, but the pressure remains elevated. By maintaining the pressure above the critical-point pressure $P_c$ throughout the process, the liquid-gas phase line 256 is never encountered along the thermodynamic path 258 and vapor lock is thereby avoided. The cryogen pressure returns to ambient pressure at point {circle around (5)} before passing through the flow controller 208, which is typically located well away from the cryoprobe 224. The cryogen may then be vented through vent 204 at substantially ambient conditions. See also U.S. Pat. No. 8,387,402 to Littrup et al. for arrangements of near critical fluid cryoablation systems, hereby incorporated by reference in its entirety.

Figure 3:
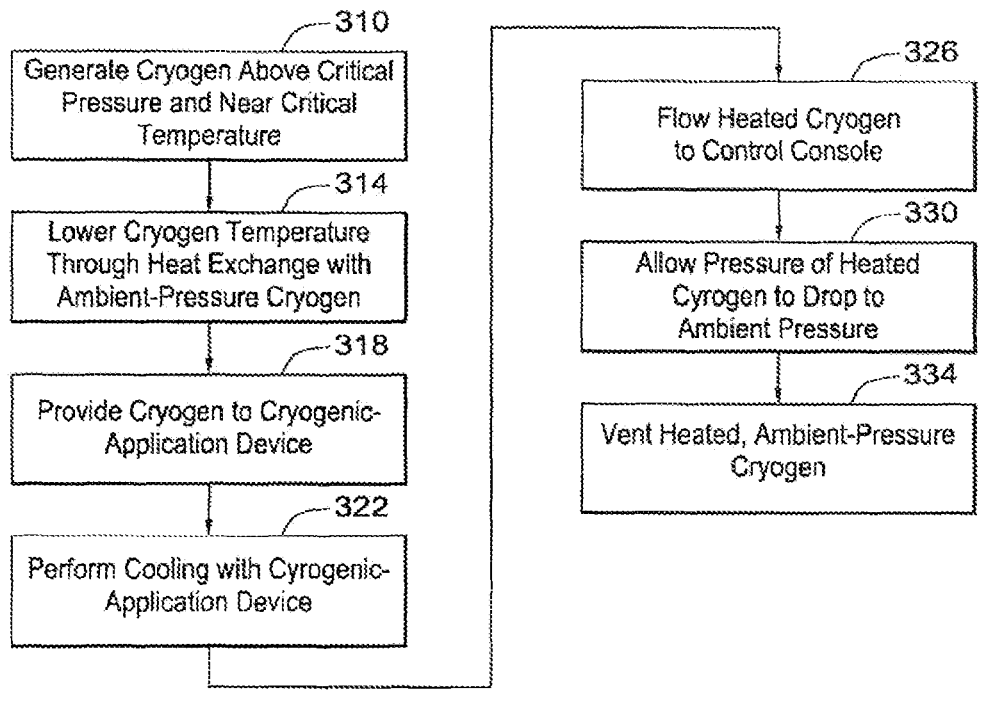
FIG. 3 provides a flow diagram of the cooling method of FIG. 2A.

A method for cooling in one embodiment in which the cryogen follows the thermodynamic path shown in FIG. 2B is illustrated with the flow diagram of FIG. 3. At block 310, the cryogen is generated with a pressure that exceeds the critical-point pressure and is near the critical-point temperature. The temperature of the generated cryogen is lowered at block 314 through heat exchange with a substance having a lower temperature. In some instances, this may conveniently be performed by using heat exchange with an ambient-pressure liquid state of the cryogen, although the heat exchange may be performed under other conditions in different embodiments. For instance, a different cryogen might be used in some embodiments, such as by providing heat exchange with liquid nitrogen when the working fluid is argon. Also, in other alternative embodiments, heat exchange may be performed with a cryogen that is at a pressure that differs from ambient pressure, such as by providing the cryogen at lower pressure to create a colder ambient.

The further cooled cryogen is provided at block 318 to a cryogenic-application device, which may be used for a cooling application at block 322. The cooling application may comprise chilling and/or freezing, depending on whether an object is frozen with the cooling application. The temperature of the cryogen is increased as a result of the cryogen application, and the heated cryogen is flowed to a control console at block 326. While there may be some variation, the cryogen pressure is generally maintained greater than the critical-point pressure throughout blocks 310-326; the principal change in thermodynamic properties of the cryogen at these stages is its temperature. At block 330, the pressure of the heated cryogen is then allowed to drop to ambient pressure so that the cryogen may be vented, or recycled, at block 334. In other embodiments, the remaining pressurized cryogen at block 326 may also return along a path to block 310 to recycle rather than vent the cryogen at ambient pressure.

Cryogen Generators

Figure 4:
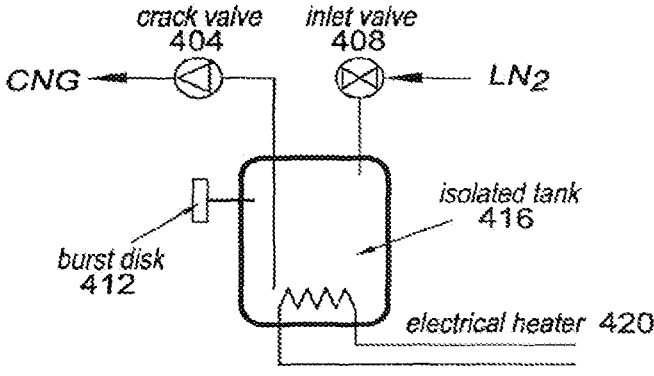
FIG. 4 is a schematic illustration of an embodiment of cryogenic cooling system.

There are a variety of different designs that may be used for the cryogen source or generator 246 in providing cryogen at a pressure that exceeds the critical-point pressure, or meets the near-critical flow criteria, to provide substantially uninterrupted cryogen flow at a pressure and temperature near its critical point. In describing examples of such designs, nitrogen is again discussed for purposes of illustration, it being understood that alternative cryogens may be used in various alternative embodiments. FIG. 4 provides a schematic illustration of a structure that may be used in one embodiment for the cryogen generator. A thermally insulated tank 416 has an inlet valve 408 that may be opened to fill the tank 416 with ambient liquid cryogen. A resistive heating element 420 is located within the tank 416, such as in a bottom section of the tank 416, and is used to heat the cryogen when the inlet valve is closed. Heat is applied until the desired operating point is achieved, i.e. at a pressure that exceeds the near-critical flow criteria. A crack valve 404 is attached to an outlet of the tank 416 and set to open at the desired pressure. In one embodiment that uses nitrogen as a cryogen, for instance, the crack valve 404 is set to open at a pressure of about 33.9 bar, about 1 bar greater than the critical-point pressure. Once the crack valve 404 opens, a flow of cryogen is supplied to the system as described in connection with FIGS. 2A and 2B above.

A burst disk 412 may also be provided consistent with safe engineering practices to accommodate the high cryogen pressures that may be generated. The extent of safety components may also depend in part on what cryogen is to be used since they have different critical points. In some instances, a greater number of burst disks and/or check valves may be installed to relieve pressures before they reach design limits of the tank 416 in the event that runaway processes develop.

During typical operation of the cryogen generator, an electronic feedback controller maintains current through the resistive heater 420 to a level sufficient to produce a desired flow rate of high-pressure cryogen into the system. The actual flow of the cryogen out of the system may be controlled by a mechanical flow controller 208 at the end of the flow path as indicated in connection with FIG. 2A. The amount of heat energy needed to reach the desired cryogen pressures is typically constant once the inlet valve 408 has been closed. The power dissipated in the resistive heater 420 may then be adjusted to keep positive control on the mechanical flow controller 208. In an alternative embodiment, the mechanical flow controller 208 is replaced with the heater controller for the cryogen generator. In such an embodiment, once the crack valve 404 opens and high-pressure cryogen is delivered to the rest of the system, the feedback controller continuously adjusts the current through the resistive heater to maintain a desired rate of flow of gaseous cryogen out of the system. The feedback controller may thus comprise a computational element to which the heater current supply and flow controller are interfaced.

Multiple Generators

Figure 5:
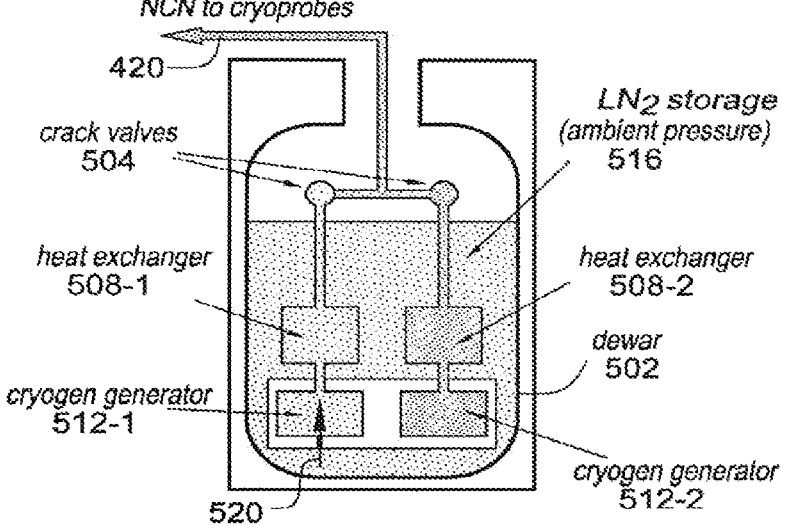
FIG. 5 is a schematic illustration of another embodiment of a cryogenic cooling system.

In another embodiment, a plurality of cryogen generators may be used to provide increased flow for specific applications. Such an embodiment is illustrated in FIG. 5 for an embodiment that uses two cryogen generators 512, although it is evident that a greater number may be used in still other embodiments. The plurality of cryogen generators 512 are mounted within an ambient-pressure cryogen Dewar 502 that contains a volume of ambient-pressure cryogen 516. Near-critical cryogen generated with the cryogen generators 512 is provided to a heat exchanger 508 that cools the cryogen in the same manner as described with respect to the heat exchanger 242 of FIG. 2A. A crack valve 504 associated with each of the cryogen generators 512 permits the high-pressure sub-cooled (i.e. cooled below the critical temperature) cryogen to be provided to cryogen-application devices along tube 420.

In some embodiments, each of the cryogen generators has a generally cylindrical shape with an internal diameter of about 30 cm and an internal height of about 1.5 cm to provide an internal volume of about one liter. The cryogen generators may conveniently be stacked, with each cryogen generator having its own independent insulating jacket and internal heater as described in connection with FIG. 4. A coil of tubing may be wrapped around the outer diameter of the stacked cryogen generators, with the output flow of high-pressure cryogen from each cryogen generator passing through a respective check valve before entering the inlet side of the coiled tubing heat exchanger. An outlet from the coil heat exchanger may advantageously be vacuum jacketed or otherwise insulated to avoid heating of the high-pressure cryogen as it flows towards the object being cooled. Such a stack of cryogen generators and the outer-coil heat exchanger may be mounted towards the bottom of a liquid-cryogen Dewar, such as a standard Dewar that holds about 40 liters of liquid $N_2$ when full. This Dewar may also be equipped with a convenient mechanism for filling the Dewar with liquid cryogen and for venting boil-off from the Dewar. In some instances, the liquid cryogen is maintained at or near ambient pressure, but may alternatively be provided at a different pressure. For instance, the liquid cryogen may be provided at a lower pressure to create a colder ambient liquid-cryogen bath temperature. In the case of liquid $N_2$, for example, the pressure may be dropped to about 98 torr to provide the cryogen at the liquid-$N_2$ slush temperature of about 63 K. While such an embodiment has the advantage of providing even lower temperatures, there may be additional engineering complexities in operating the liquid-cryogen Dewar below ambient pressure.

Operation of the multiple-cryogen-generator embodiments may advantageously be configured to provide a substantially continuous supply of high-pressure cryogen to the cryogenic device. The ambient liquid-cryogen 516 is used as a supply for a depleted cryogen generator 512, with the depleted cryogen generator 512 being refilled as another of the cryogen generators 512 is used to supply high-pressure or near-critical cryogen. Thus, the example in FIG. 5 with two cryogen generators is shown in an operational state where the first of the cryogen generators 512-1 has been depleted and is being refilled with ambient liquid cryogen 516 by opening its inlet valve to provide flow 520. At the same time, the second cryogen generator 512-2 has a volume of liquid cryogen that is being heated as described so that cryogen is being delivered as near-critical cryogen through its outlet crack valve 504. When the second cryogen generator 512-2 empties, the fill valve of the first cryogen generator 512-1 will be closed and its heater brought to full power to bring it to the point where it provides near-critical cryogen through its check valve. The inlet valve of the second cryogen generator 512-2 is opened so that it may engage in a refill process, the two cryogen generators 512 thereby having exchanged roles from what is depicted in FIG. 5.

The two cryogen generators 512 operate out of phase in this way until the entire Dewar 502 of ambient liquid cryogen is depleted, providing a substantially continuous flow of near-critical cryogen to the cryogenic application devices until that time. The system is thus advantageously scalable to meet almost any intended application. For example, for an application defined by a total cooling time and a rate at which cryogen is consumed by providing a Dewar of appropriate size to accommodate the application. As will be noted later, the cooling capacity of near-critical liquid $N_2$ allows efficient consumption of cryogen for maximal operation times and scaling of near-critical cryogen generators to total freeze time requirements dictated by specific application needs. For instance, the inventors have calculated that medical cryogenic freezing applications may use near-critical cryoprobes that consume about two liters of ambient liquid $N_2$ per instrument per hour.

Handheld Cryoablation Instrument

Figure 6:
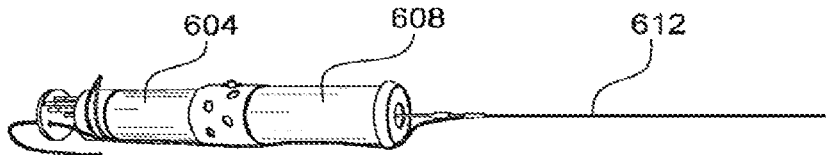
FIG. 6 is an illustration of an embodiment of a self-contained handheld
device.

A self-contained handheld cryoablation instrument is shown in FIG. 6. The integrated handheld instrument is especially suitable for use in applications involving a relatively brief cryogenic cooling, such as dermatology and interstitial low-volume freeze applications (e.g., treatment of breast fibroadenomas, development of cryo-immuno-therapy). The structure of such an instrument is substantially as described in connection with FIG. 2A, with the components provided as a small self-contained unit. In particular, a relatively small cryogen generator 604 is connected in series with a small ambient liquid-cryogen tank 608, and a mounted cryogenic device 612 (e.g., without limitation, needles, probes, and catheters). In the example shown in FIG. 6, the cryogenic device is a cryosurgical device that is permanently mounted to the instrument, although other types of cryogenic devices may be used in different embodiments. The self-contained handheld instrument may be provided as a disposable single-use instrument or may be rechargeable with liquid cryogen in different embodiments. The cryogen generator 604 and ambient liquid-cryogen tank 608 are vacuum jacketed or otherwise thermally insulated from their surrounding environment and from each other. For purposes of illustration, the instrument shown in FIG. 6 has the outer tube that holds the cryogen generator 604 and liquid-cryogen tank 608 under vacuum removed. Preferably, a switch is provided that allows an operator to control a small heater in the cryogen generator. The activation of the heater results in a flow of near-critical cryogen through set flow impedances that may be customized for a particular cooling task as described above. The flow of near-critical cryogen may continue until a reservoir of such cryogen within the instrument is expended, after which the instrument may be disposed of or recharged for future use.

The handheld-instrument embodiments may be considered to be part of the continuum of scalability permitted by the disclosure. In particular, there is not only the option of providing sufficient near-critical or high-pressure cryogen for high-volume clinical or other uses, but also for short-duration low-volume uses. Over the full range of this continuum, operation is possible with very small cryogenic-device sizes, i.e. less than 1 mm, because there is no barrier presented by the phenomenon of vapor lock. For example, the ability to operate with small device sizes enables a realistic arrangement in which small rechargeable or disposable liquid-cryogen cartridges are provided as a supply, removing the need for large, inconvenient cryogenic systems. For instance, in the context of a medical application such as in a clinical setting for nerve ablation, or pain treatment, a small desktop Dewar of liquid $N_2$ may be used to provide liquid $N_2$ for refilling multiple cartridges as needed for nerve ablation. For a typical volume in such a clinical setting, the desktop Dewar would require recharging perhaps once a week to provide enough liquid for refilling the cartridges for use that week. Similar benefits may be realized with embodiments of the disclosure in industrial settings, such as where short-term cooling is provided by using disposable cartridges as needed. A minor accommodation for such applications would provide appropriate venting precautions for the tiny amount of boil-off that is likely to occur, even with well-insulated and/or pressurized cartridges. Embodiments of the disclosure thus enable an enhanced scope of cryogenic cooling options for numerous types of applications.

Figure 8:
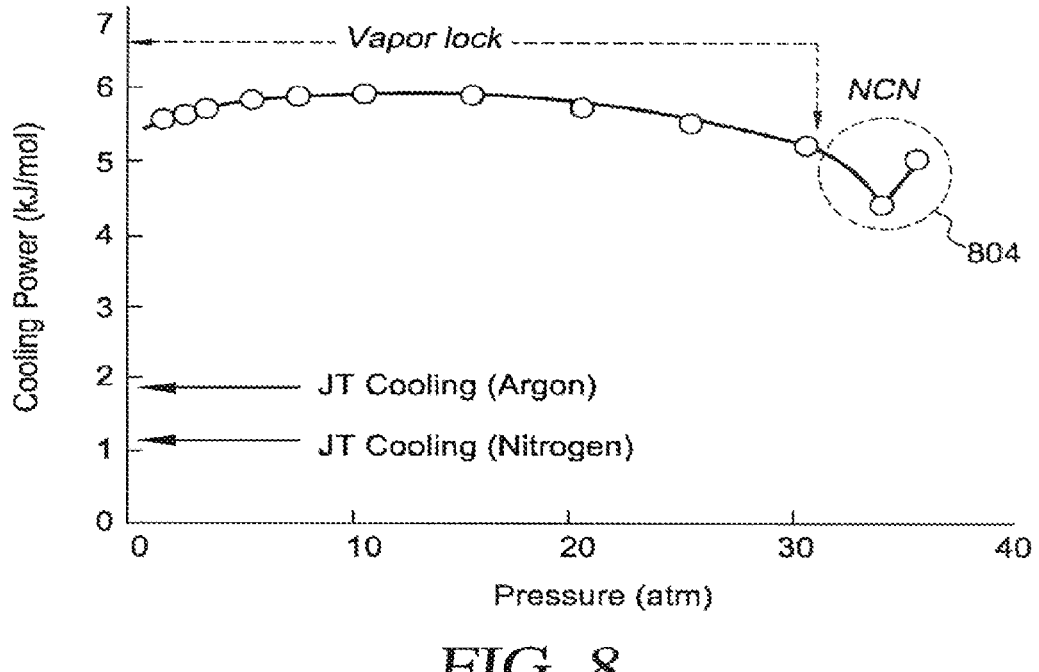
FIG. 8 provides a graphical comparison of cooling power for different embodiments of cryogenic cooling processes.

Embodiments of the disclosure provide increased cooling power when compared with simple-flow cryogen cooling or with Joule-Thomson cooling, with one consequence being that the need for multiple high-pressure tanks of cryogen is avoided even without recycling processes. A comparison is made in FIG. 8 of the cooling power per mole of cryogen for the three different cooling systems. The top curve corresponds to the cooling cycle described herein in connection with FIG. 2B using $N_2$ as the cryogen, while the bottom two points identify the cooling power for Joule-Thomson processes that use argon and nitrogen as cryogens. The Joule-Thomson results represent maximum values for those processes because they were determined for perfect counter-flow heat exchange; this heat exchange becomes very inefficient as the probe diameter is reduced.

The presented results note that vapor lock of liquid $N_2$ may occur at lower pressures, but can be avoided in the circled region 804 when the process meets the near-critical conditions for pressures near the critical-point pressure for $N_2$ of 33.94 bar. As previously noted, vapor lock may be avoided at near-critical flow conditions, although the efficiency of the process is improved when the pressure is near the critical-point pressure. The results illustrate that cooling cycles provided according to embodiments of the disclosure are more than five times as efficient as idealized Joule-Thomson cycles. Since the efficiency of embodiments that use pressures above the critical-point pressure is not substantially affected by changes in probe size, the cooling power per gram is often more than ten times greater than the cooling power for Joule-Thomson cycles. This greater efficiency is manifested by the use of substantially less, i.e. ⅕th-⅒oth, of the exhaust gas flow, making the process much quieter, less disruptive, and without the need for bulky multiple-tank replacements.

Multi-Tubular Cryoablation Catheter

Figures 9, 10:
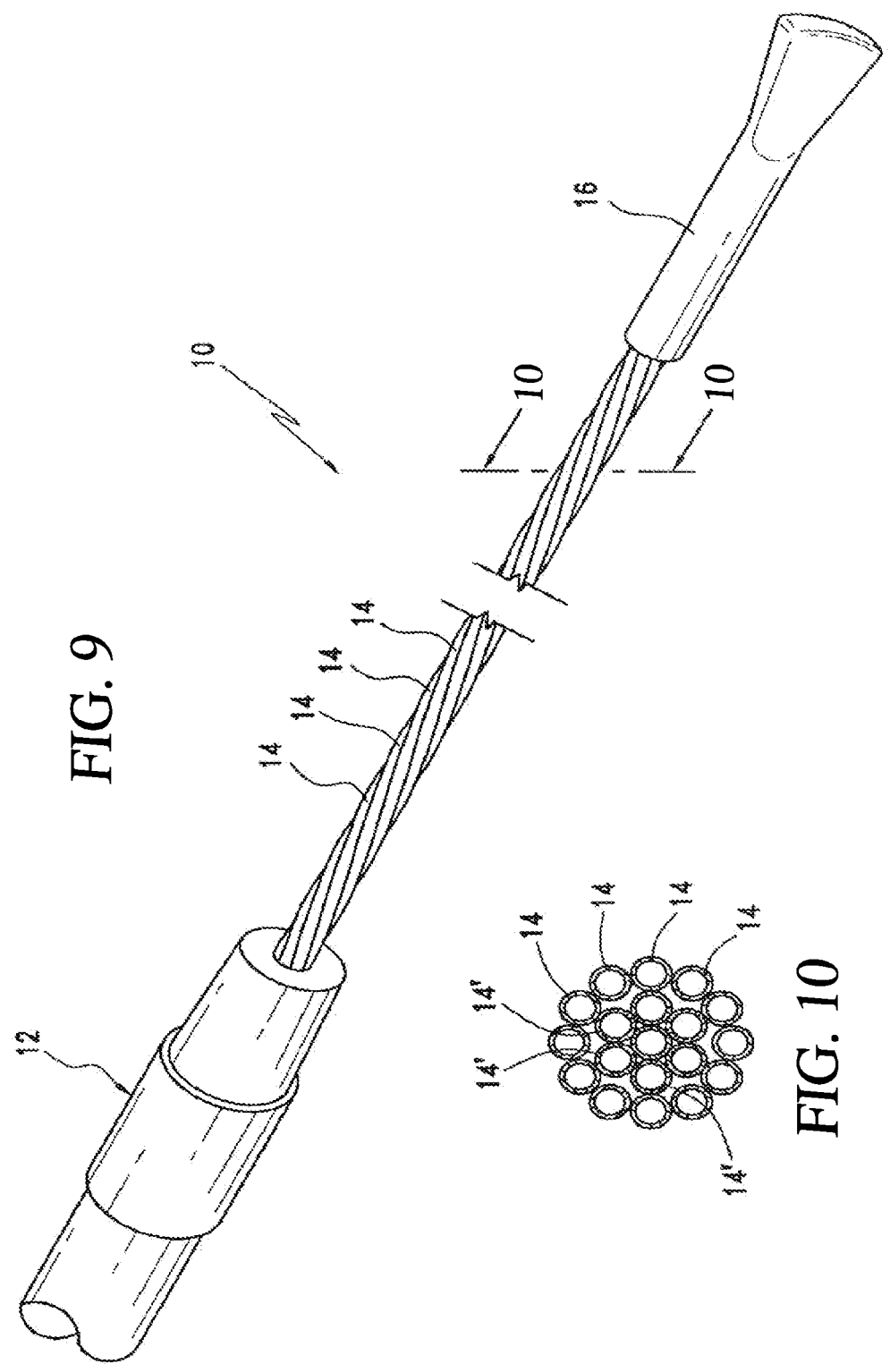
FIG. 9 is a perspective view of an embodiment of a cryoprobe.
FIG. 10 is a view taken along line 10-10 of FIG. 9.

FIGS. 9 and 10 illustrate a flexible multi-tubular cryoprobe 10. The cryoprobe 10 includes a housing 12 for receiving an inlet flow of near critical cryogenic fluid from a fluid source (not shown) and for discharging an outlet flow of the cryogenic fluid. A plurality of fluid transfer tubes 14, 14' are securely attached to the housing 12. These tubes include a set of inlet fluid transfer tubes 14 for receiving the inlet flow from the housing; and, a set of outlet fluid transfer tubes 14' for discharging the outlet flow to the housing 12. Each of the fluid transfer tubes 14, 14' is formed of material that maintains flexibility in a full range of temperatures from −200° C. to ambient temperature. Each fluid transfer tube has an inside diameter in a range of between about 0.10 mm and 1.0 mm (preferably between about 0.20 mm and 0.50 mm) Each fluid transfer tube has a wall thickness in a range of between about 0.01 mm and 0.30 mm (preferably between about 0.02 mm and 0.10 mm) An end cap 16 is positioned at the ends of the fluid transfer tubes 14, 14' to provide fluid transfer from the inlet fluid transfer tubes 14 to the outlet fluid transfer tubes 14'.

The tubes 14, 14' are preferably formed of annealed stainless steel or a polyimide, preferably Kapton® polyimide. It is preferable that the material maintains flexibility at a near critical temperature. By flexibility, it is meant the ability of the cryoprobe to be bent in the orientation desired by the user without applying excess force and without fracturing or resulting in significant performance degradation.

The cryogenic fluid utilized is preferably near critical nitrogen. However, other near critical cryogenic fluids may be utilized such as argon, neon, helium or others.

The fluid source for the cryogenic fluid may be provided from a suitable mechanical pump or a non-mechanical critical cryogen generator as described above. Such fluid sources are disclosed in, for example, U.S. patent application Ser. No. 10/757,768 which issued as U.S. Pat. No. 7,410,484, on Aug. 12, 2008 entitled "CRYOTHERAPY PROBE", filed Jan. 14, 2004 by Peter J. Littrup et al.; U.S. patent application Ser. No. 10/757,769 which issued as U.S. Pat. No. 7,083,612 on Aug. 1, 2006, entitled "CRYOTHERAPY SYSTEM", filed Jan. 14, 2004 by Peter J. Littrup et al.; U.S. patent application Ser. No. 10/952,531 which issued as U.S. Pat. No. 7,273,479 on Sep. 25, 2007 entitled "METHODS AND SYSTEMS FOR CRYOGENIC COOLING" filed Sep. 27, 2004 by Peter J. Littrup et al. U.S. Pat. Nos. 7,410,484, 7,083,612 and 7,273,479 are incorporated herein by reference, in their entireties, for all purposes.

The endcap 16 may be any suitable element for providing fluid transfer from the inlet fluid transfer tubes to the outlet fluid transfer tubes. For example, endcap 16 may define an internal chamber, cavity, or passage serving to fluidly connect tubes 14, 14'.

There are many configurations for tube arrangements. In one class of embodiments the tubes are formed of a circular array, wherein the set of inlet fluid transfer tubes comprises at least one inlet fluid transfer tube defining a central region of a circle and wherein the set of outlet fluid transfer tubes comprises a plurality of outlet fluid transfer tubes spaced about the central region in a circular pattern. In the configuration shown in FIG. 10, the tubes 14, 14' fall within this class of embodiments.

During operation, the cryogen fluid arrives at the cryoprobe through a supply line from a suitable nitrogen source at a temperature close to −200° C., is circulated through the multi-tubular freezing zone provided by the exposed fluid transfer tubes, and returns to the housing.

In embodiments, the nitrogen flow does not form gaseous bubbles inside the small diameter tubes under any heat load, so as to not create a vapor lock that limits the flow and the cooling power. By operating at the near critical condition the vapor lock is eliminated as the distinction between the liquid and gaseous phases disappears.

Embodiments of the present disclosure provides a substantial increase in the heat exchange area between the cryogen and tissue, over prior art cryoprobes, by this multi-tubular design. Depending on the number of tubes used, the present cryoprobes can increase the contact area several times over previous cryoprobes having similarly sized diameters with single shafts.

Figures 11, 12, 13:
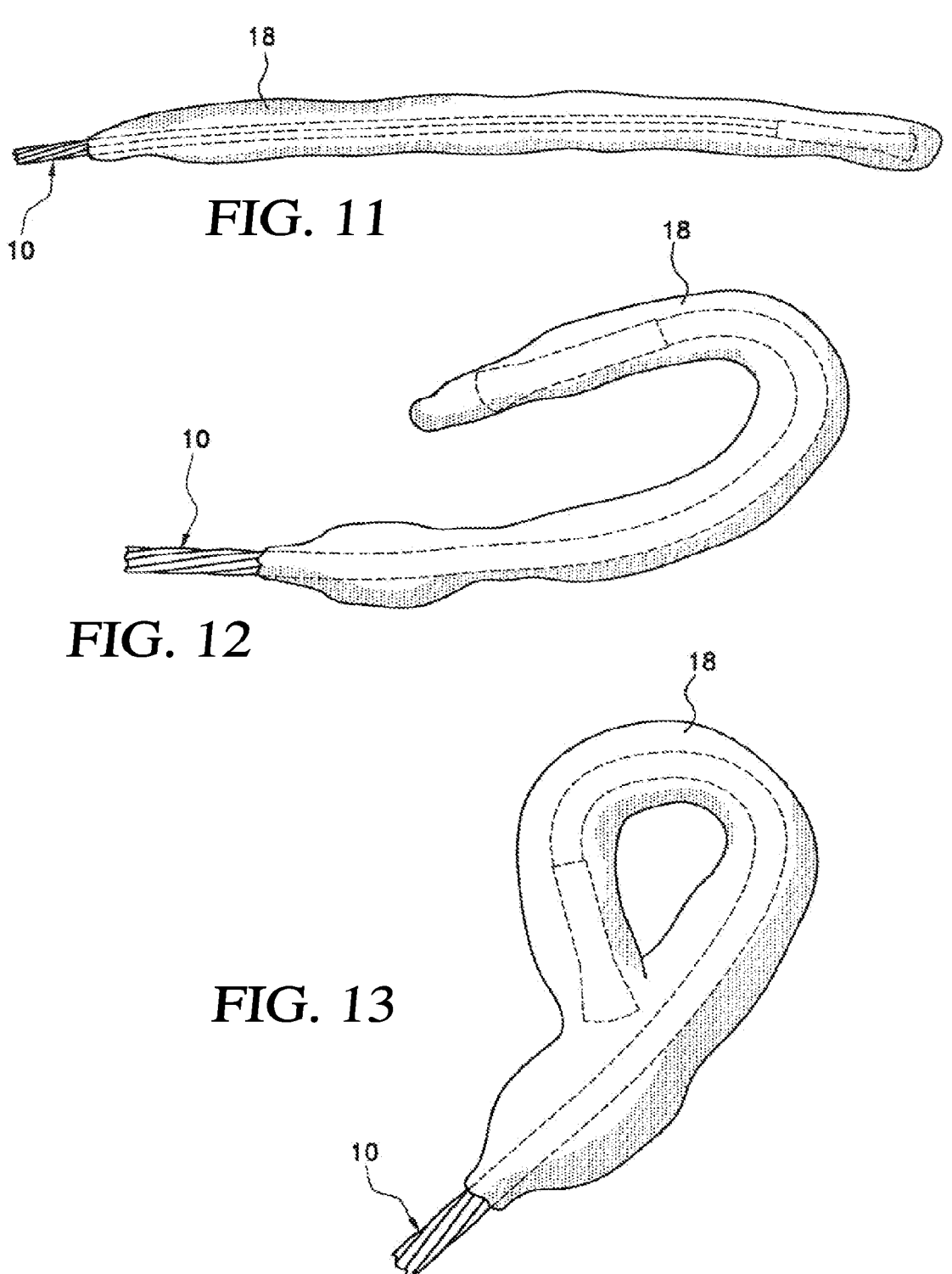
FIG. 11 is a perspective view of an embodiment of a cryoprobe of FIG. 9 operated to generate an iceball.
FIG. 12 is a perspective view of an embodiment of a cryoprobe of FIG. 9 that is bent to approximately 180° to form a commensurately bent iceball.
FIG. 13 illustrates an embodiment of a cryoprobe bent so as to form a loop.

As can be seen in FIG. 11, an iceball 18 is generated about the cryoprobe 10. Referring now to FIG. 12, it can be seen that an iceball 18 can be created in the desired shape by bending the cryoprobe in the desired orientation. A complete iceball 18 loop can be formed, as shown in FIG. 13.

Figures 14, 15:
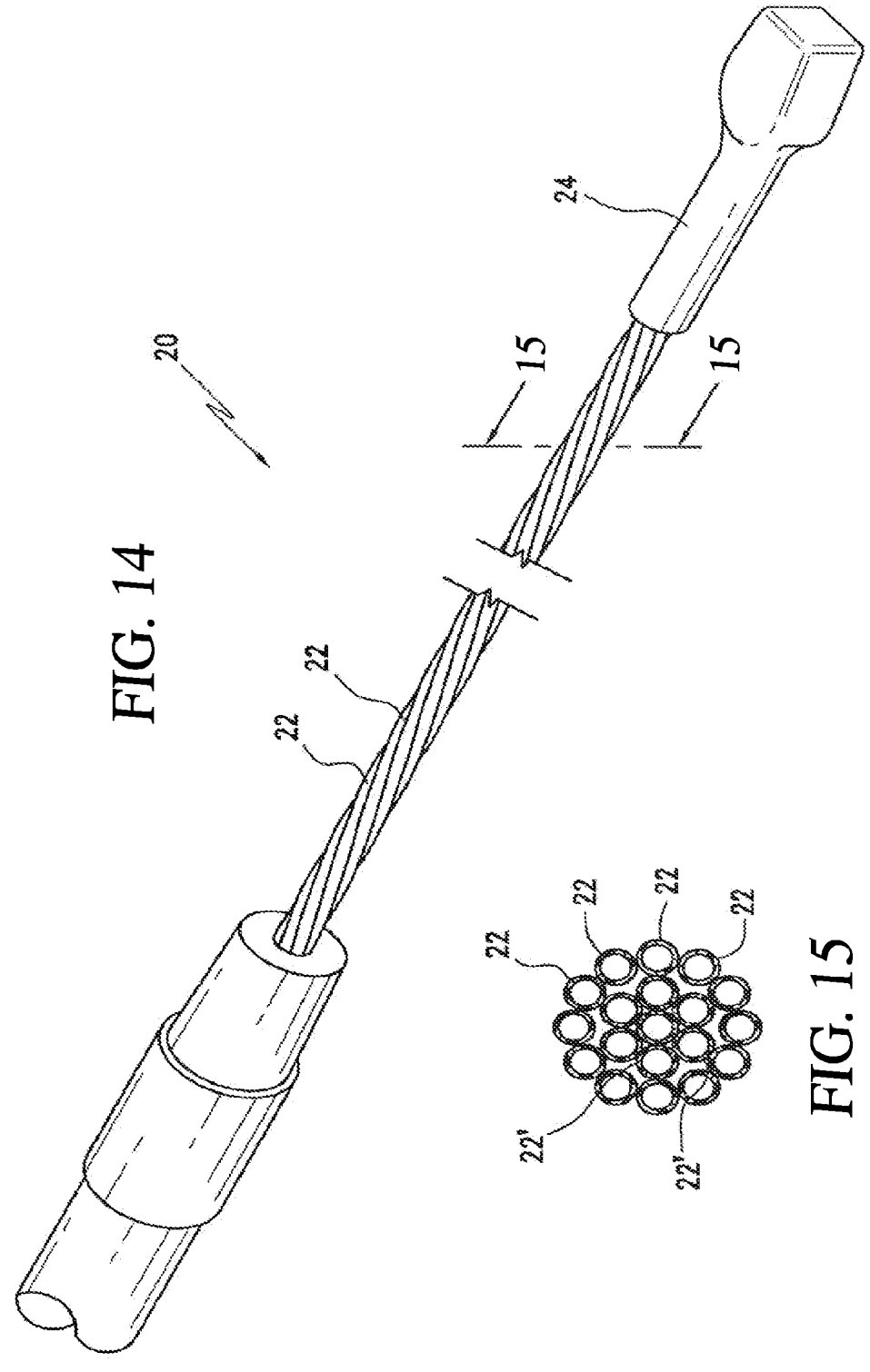
FIG. 14 is a perspective view of another embodiment of a cryoprobe having a flexible distal section.
FIG. 15 is a view taken along line 15-15 of FIG. 14.

Referring now to FIG. 14, a cryoprobe 20 is illustrated, which is similar to the embodiment of FIG. 9, however, with this embodiment a polyimide material is used to form the tubes 22, 22'. Furthermore, this figure illustrates the use of a clamp 24 as an endcap.

Figures 16, 17, 18, 19:
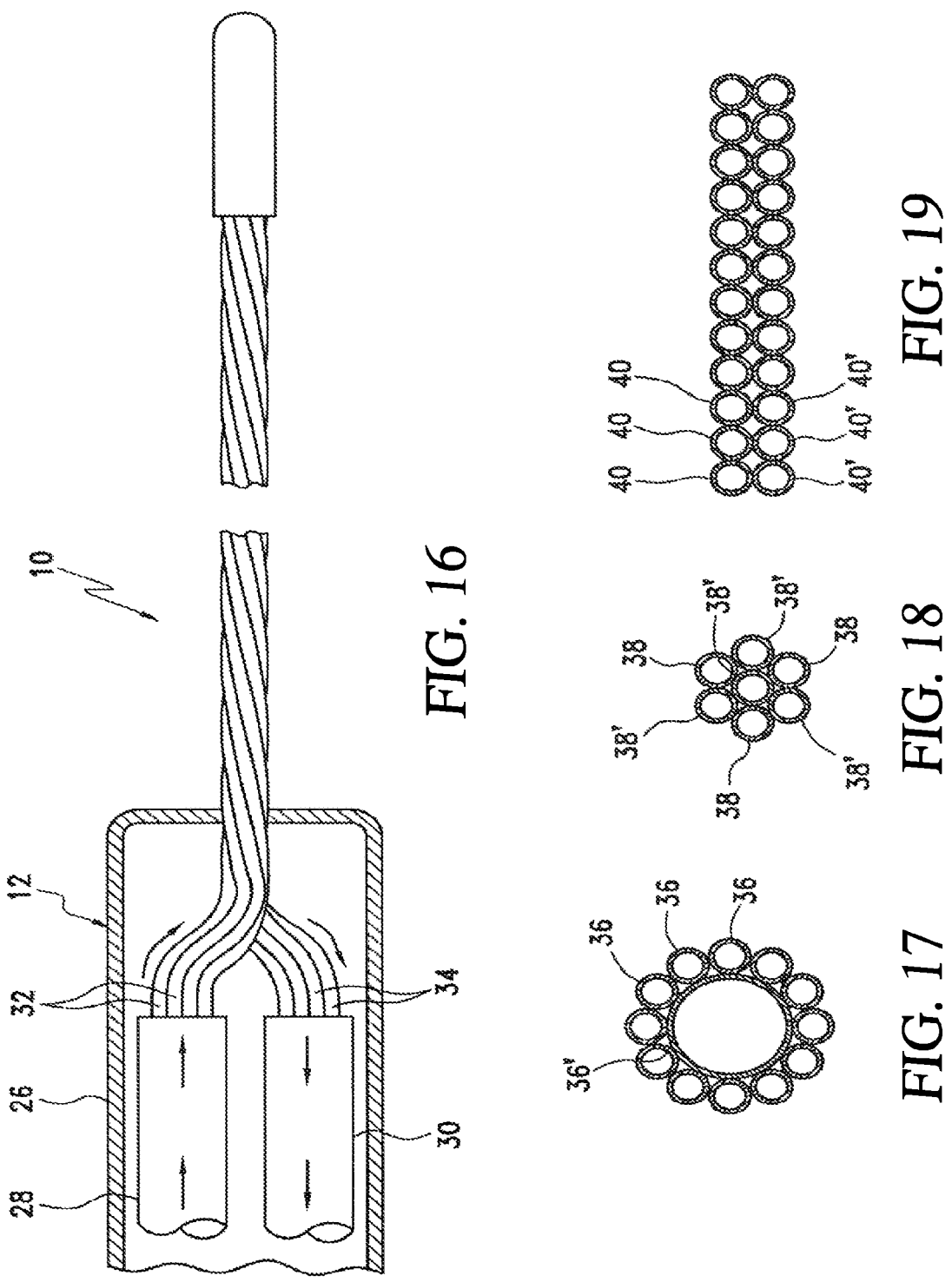
FIG. 16 is a side view of another embodiment of a cryoprobe including a handle having a inlet shaft and outlet shaft therein.
FIGS. 17-19 are schematic cross sectional views showing example alternative arrangements of fluid transfer tubes.

Referring now to FIG. 16, one embodiment of the housing 12 of a cryoprobe 10 is illustrated. The housing 12 includes a handle 26 that supports an inlet shaft 28 and an outlet shaft 30. The inlet shaft 28 is supported within the handle 26 for containing proximal portions of the set of inlet fluid transfer tubes 32. The outlet shaft 30 is supported within the handle 26 for containing proximal portions of the set of outlet fluid transfer tubes 34. Both of the shafts 28, 30 include some type of thermal insulation, preferably a vacuum, to isolate them.

Referring now to FIGS. 17-19 various configurations of tube configurations are illustrated. In FIG. 17 a configuration is illustrated in which twelve inlet fluid transfer tubes 36 circumscribe a single relatively large outlet fluid transfer tube 36'. In FIG. 18, three inlet fluid transfer tubes 38 are utilized with four outlet fluid transfer tubes 38'. In FIG. 19, a plane of inlet fluid transfer tubes 40 are formed adjacent to a plane of outlet of fluid transfer tubes 40'.

In an example, an annealed stainless steel cryoprobe was utilized with twelve fluid transfer tubes. There were six inlet fluid transfer tubes in the outer circumference and six outlet fluid transfer tubes in the center. The tubes were braided as shown in FIG. 9. The length of the freeze zone was 6.5 inches. Each fluid transfer tube had an outside diameter of 0.16 inch and an inside diameter 0.010 inch. The diameter of the resultant array of tubes was 0.075 inch. After a one minute freeze in 22° C. water and near-critical (500 psig) nitrogen flow of approximately 20 STP l/min, ice covered the entire freeze zone of the flexible cryoprobe with an average diameter of about 0.55 inch. After four minutes the diameter was close to 0.8 inch. The warm cryoprobe could be easily bent to any shape including a full loop of approximately 2 inch in diameter without any noticeable change in its cooling power.

In another example, a polyimide cryoprobe was utilized with twenty-one fluid transfer tubes. There were ten inlet fluid transfer tubes in the outer circumference and eleven outlet fluid transfer tubes in the center. The tubes were braided. The length of the freeze zone was 6.0 inches. Each fluid transfer tube had an outside diameter of 0.0104 inch and an inside diameter 0.0085 inch. Each tube was pressure rated for about 1900 psig (working pressure 500 psig). The average diameter of the flexible portion of the cryoprobe was 1.15 mm (0.045 inch). The cryoprobe was extremely flexible with no perceivable "memory" in it. It bent by its own weight of just 1 gram and easily assumed any shape with a bending radius as little as 0.1 inch, including a 1 inch diameter "knot". A full loop was created with the cryoprobe. After a one minute freeze in 22° C. water and near critical (500 psig) nitrogen flow of approximately 20 STP l/min, ice covered the entire freeze zone of the flexible cryoprobe with an average diameter of 0.65 inch and in two minutes it closed the entire 1 inch hole inside the loop. See also, U.S. Publication No, 2011/0040297 to Babkin et al., hereby incorporated by reference in its entirety, for additional cryoprobe and catheter designs.

Cryoablation Catheter with Fluid Filled Protective Cover

Figure 20A:
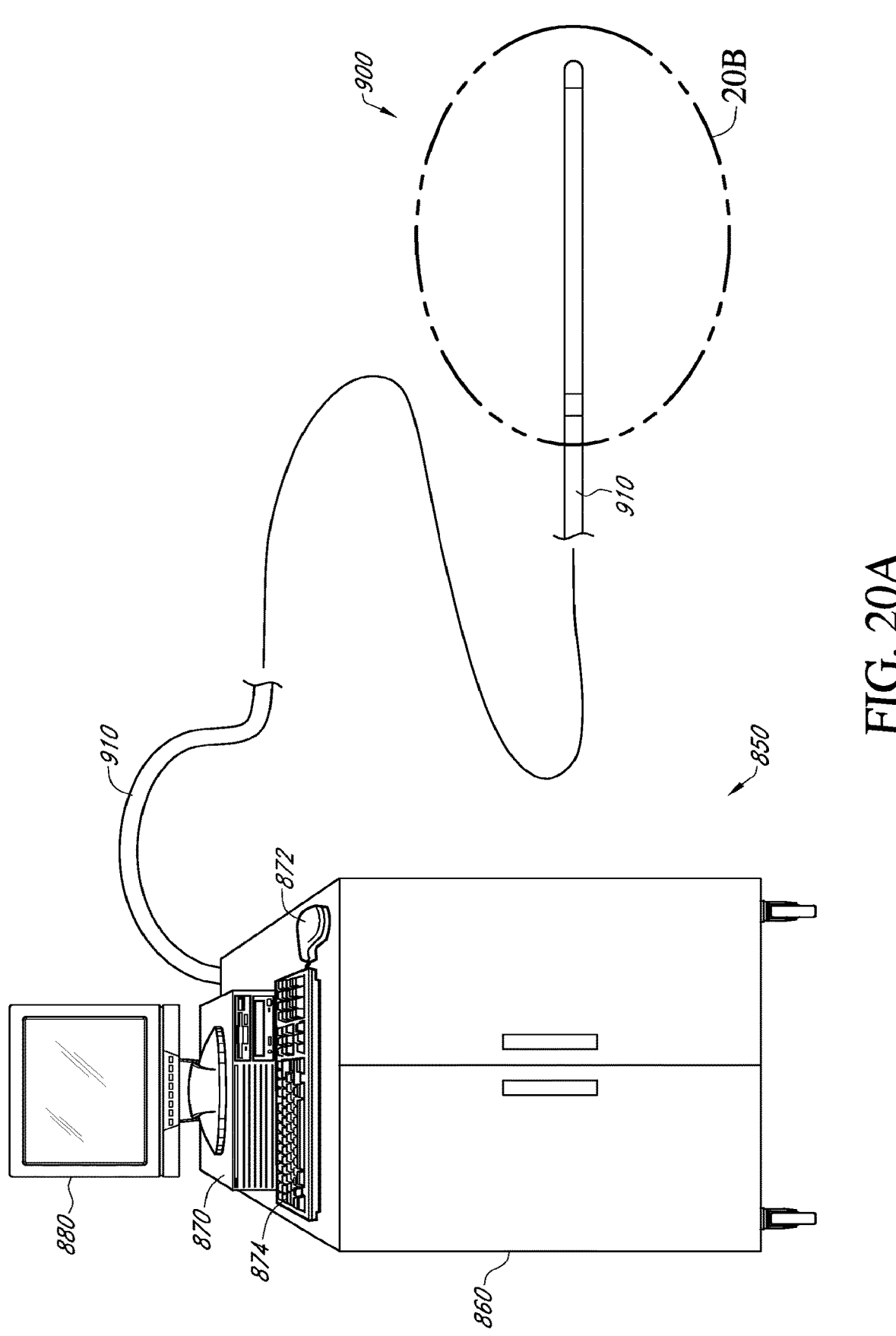
FIG. 20A is an illustration of an embodiment of a cryoablation system including an embodiment of a cryoablation catheter.

FIG. 20A illustrates a cryoablation system 850 having a cart or console 860 and a cryoablation catheter 900 detachably connected to the console via a flexible elongate tube 910. The cryoablation catheter 900, which shall be described in more detail below in connection with FIG. 20B, includes a protective cover to contain leaks of the cryogen in the event one of the fluid transport tubes is breached. Although a leak is not expected or anticipated in any of the fluid delivery transport tubes, the protective cover provides an extra or redundant barrier that the cryogen would have to penetrate in order to escape the catheter during a procedure.

The console 860 may include a variety of components (not shown) such as, for example, a generator, controller, tank, valve, pump, etc. A computer 870 and display 880 are shown in FIG. 20A positioned on top of cart for convenient user operation. Computer may include a controller, or communicate with an external controller to drive components of the cryoablation systems such as a pump, valve or generator. Input devices such as a mouse 872 and a keyboard 874 may be provided to allow the user to input data and control the cryoablation devices.

In embodiments computer 870 is configured or programmed to control cryogen flowrate, pressure, and temperatures as described herein. Target values and real time measurement may be sent to, and shown, on the display 880.

Figure 20B:
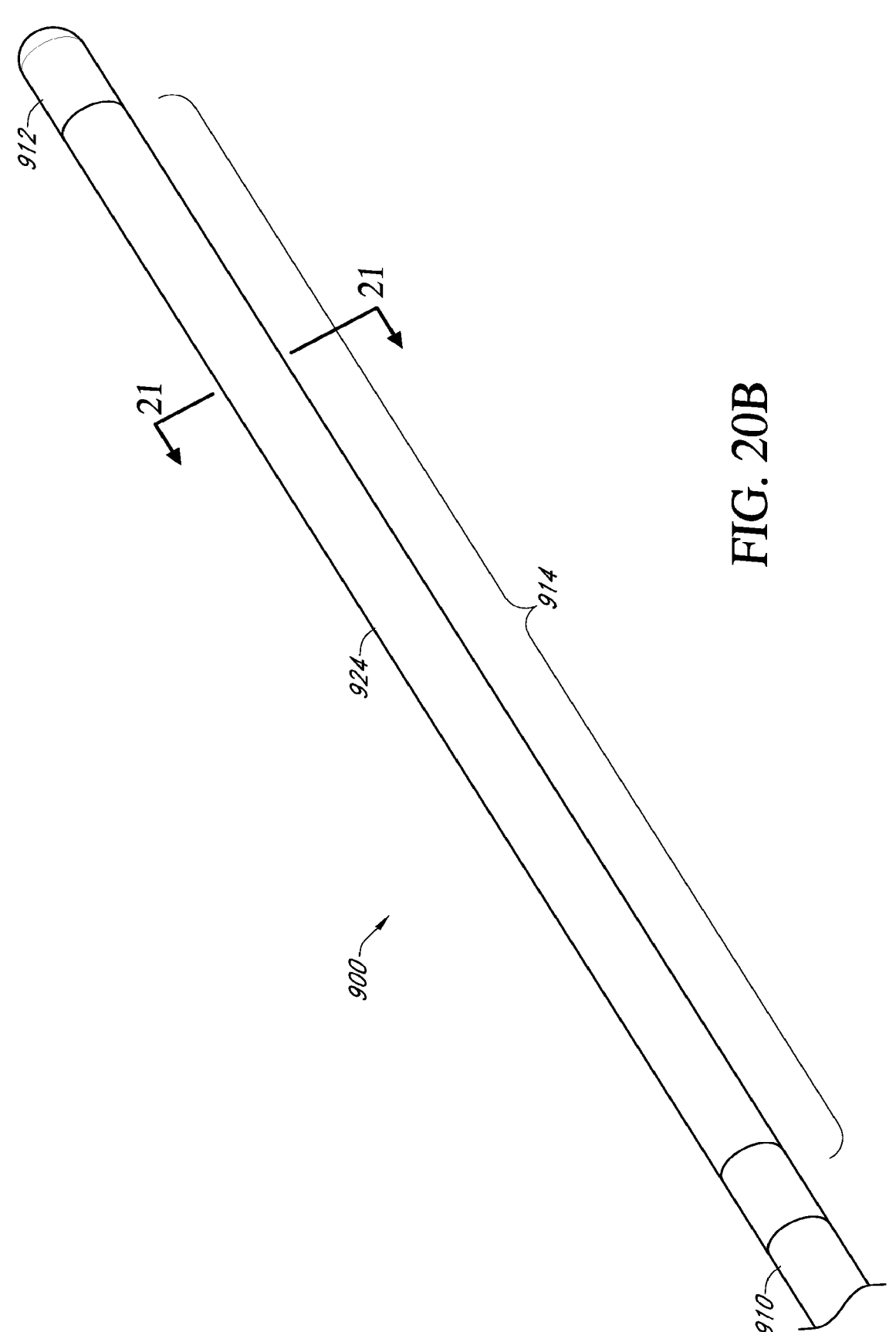
FIG. 20B is an enlarged perspective view of a distal section of an embodiment of a cryoablation catheter shown in FIG. 20A.

FIG. 20B shows an enlarged view of distal section of cryoablation apparatus 900. The distal section 900 is similar in design to the cryoprobes described above except that treatment region 914 includes a flexible protective cover 924. Cover 924 is shown being tubular or cylindrically shaped and terminates at distal tip 912. As described herein, the cooling region 914 contains a plurality of fluid delivery and fluid return tubes to transport a cooling fluid through the treatment region 914 causing heat to be transferred/removed from the target tissue. In embodiments, the fluid is transported through the tube bundle under physical conditions near the fluid's critical point in the phase diagram. The cover serves to, amongst other things, contain the cooling fluid and prevent it from escaping from the catheter in the event a leak forms in one of the delivery tubes.

Figure 21B:
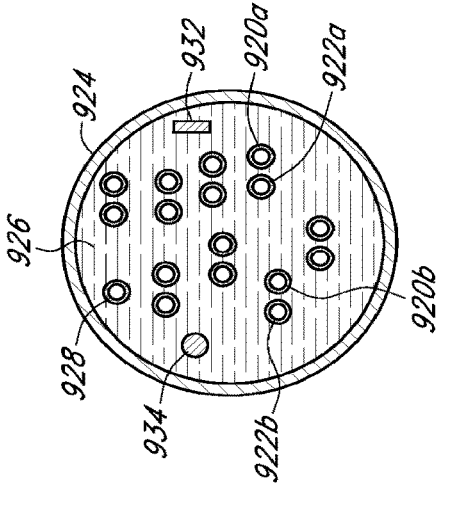
FIGS. 21A-21C are cross sectional views of various tube configurations of an embodiment of a catheter shown in FIG. 20B taken along line 21-21.
Figure 21C:
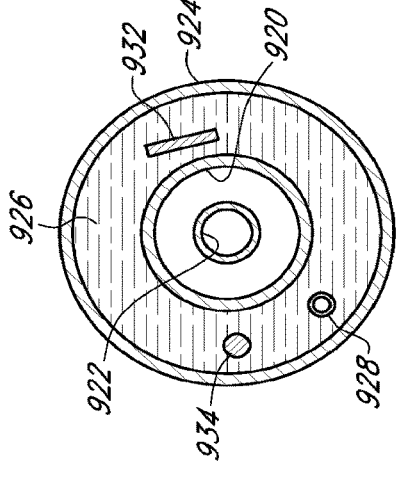
Figure 21A:
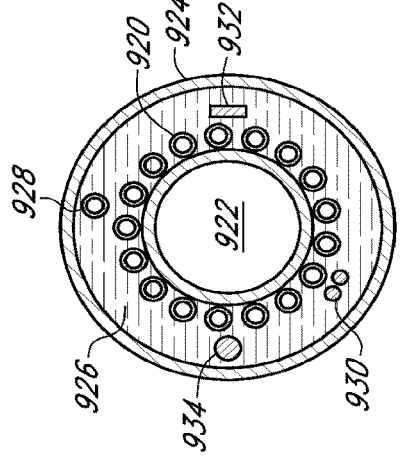

FIG. 21A shows a cross sectional view of the distal treatment section 900 taken along line 21-21. A plurality of fluid return tubes 920 are shown circumferentially surrounding fluid delivery tube 922.

A gap or space is shown between the fluid return tubes and an inner surface of the cover 924. Gap is filled with a thermally conductive fluid or media 926. An example of a thermally conductive fluid is water.

In operation, when the catheter can be placed against the target tissue to be cooled, heat is transferred from the tissue, through cover 924, through thermally conductive liquid 926, and to the fluid or cryogen being transported in fluid return tubes. If a breach in the fluid delivery or fluid return tubes occurs, the cold fluid is contained by cover 924.

FIG. 21A shows media line 928. Media line 928 delivers the space-filling thermally conductive media such as water to the gap between the tube bundle and the cover 924. The gel or media is preferably non-circulating. Media line 928 is preferably a flexible tubular structure. Line 928 may terminate at a location anywhere along the length of the cover 924. Line 928 extends proximally to a location accessible by a fluid supply such as a syringe or pump. Line may include an adapter or fluid connector to join a syringe thereto.

Additionally, a pressure sensor or gauge may be incorporated with the fluid line to monitor pressure of the thermally conductive media 926. In embodiments, should a change in pressure occur above a threshold limit, ablation is halted.

A wide range of sensors may be incorporated into the cryoablation catheter. Temperature wires 930 (e.g., thermocouple) are shown in FIG. 21A to measure a temperature of the thermally conductive fluid 926. However, more or less wires may be added to measure additional parameters such as temperature of the cover, resistivity for mapping electrical signals, and other data.

FIG. 21A shows pull wire 934 which serves to articulate, controllably deflect or steer the catheter. Pull wire 934 extends from a location in the proximal section of the catheter (not shown) to a location in the distal tip section of the catheter. The pull wire is fixed at a distal point or location (e.g., to the end cap 912). When the proximal end of the pull wire is manipulated (e.g., pulled) the distal section of the catheter 914 can bend in a controlled predictable amount. Spine element 932 is shown in FIG. 21A which serves to bias bending of the distal section in one direction or another.

The shapes and materials of the spine element and pull wire may vary. For example, the spine element may be a ribbon or flat wire of steel. Pull wire may have a circular cross section as shown. Additional steering means and mechanisms are described in, for example, U.S. Pat. No. RE 34,502 and U.S. patent application Ser. No. 09/157,055 (filed Sep. 18, 1998), Ser. No. 09/130,359 (filed Aug. 7, 1998), and Ser. No. 08/924,611 (filed Sep. 5, 1997), which are incorporated herein by reference in their entirety.

The footprint or arrangement of the fluid tubes and fluid return tube may vary widely. For example, FIG. 21B shows another arrangement in which there are an equal number and size of tubular elements. Tubular elements are arranged in a side by side or one-to-one configuration. Each fluid return tube 920a, 920b, . . . can be adjacent and parallel to a corresponding fluid delivery tube 922a, 922b, . . . . Another tube footprint is shown in FIG. 21C. Fluid return tube 920 coaxially surrounds inner fluid delivery tube 922. Cover 924 coaxially surrounds fluid return tube.

Figure 22:
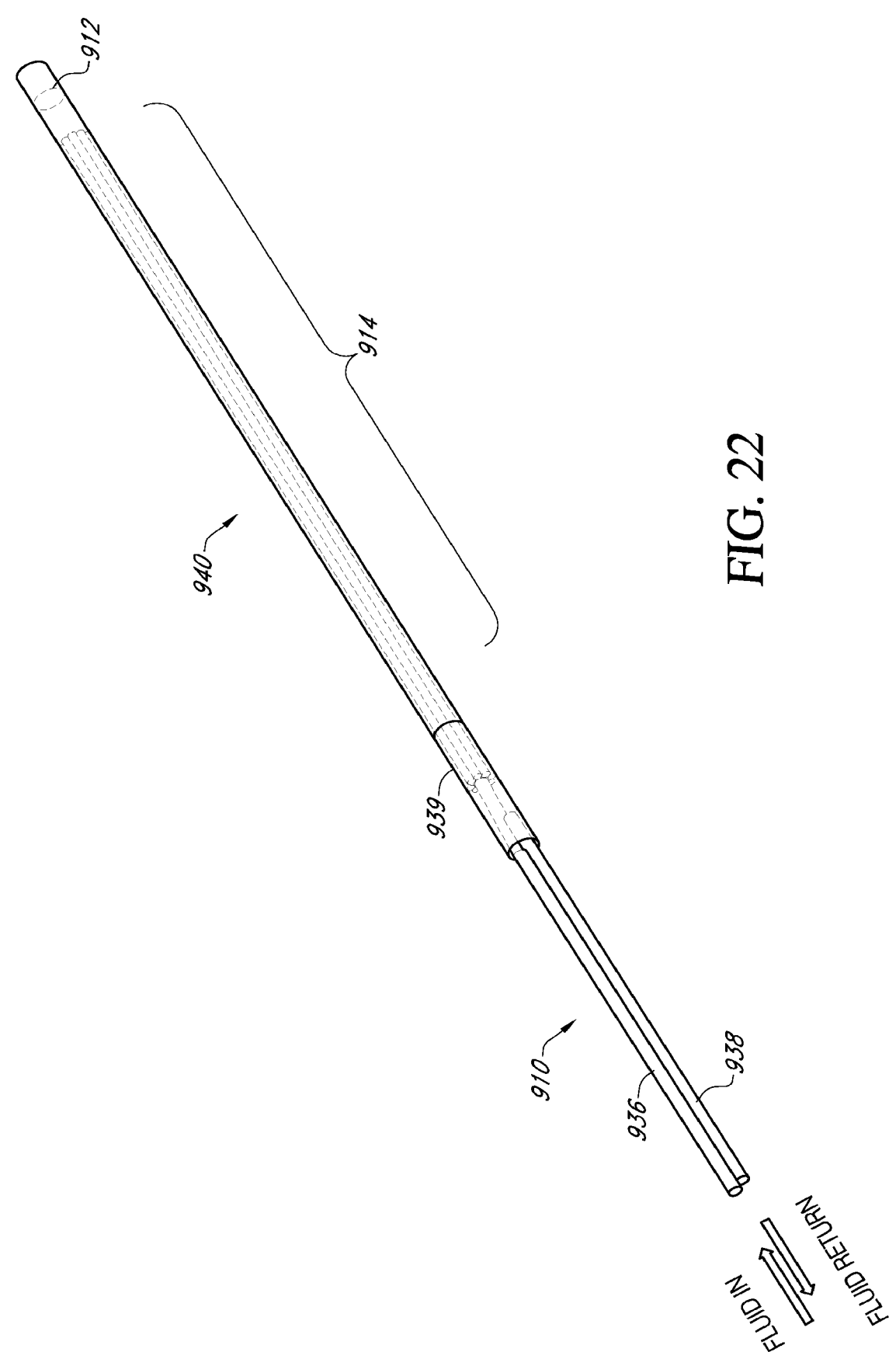
FIG. 22 is a perspective view of the distal section of an embodiment of a cryoablation catheter of FIG. 20 with the cover removed.

FIG. 22 shows a catheter and its exterior layer removed for purposes of illustration. In particular, intermediate region 910 includes fluid-in conduit 936 and fluid-return conduit 938 which are substantially larger in diameter than the individual tubular members in the treatment section 914.

The fluid delivery tubes are fluidly connected to the fluid-in conduit 936 and the fluid return tubes are fluidly connected to the fluid-return conduit 936. A sleeve member 939 is shown encompassing this transition region. An enclosed chamber is provided at the distal tip 912 to redirect fluid from the fluid delivery tubes into the fluid return tubes.

Figure 23:
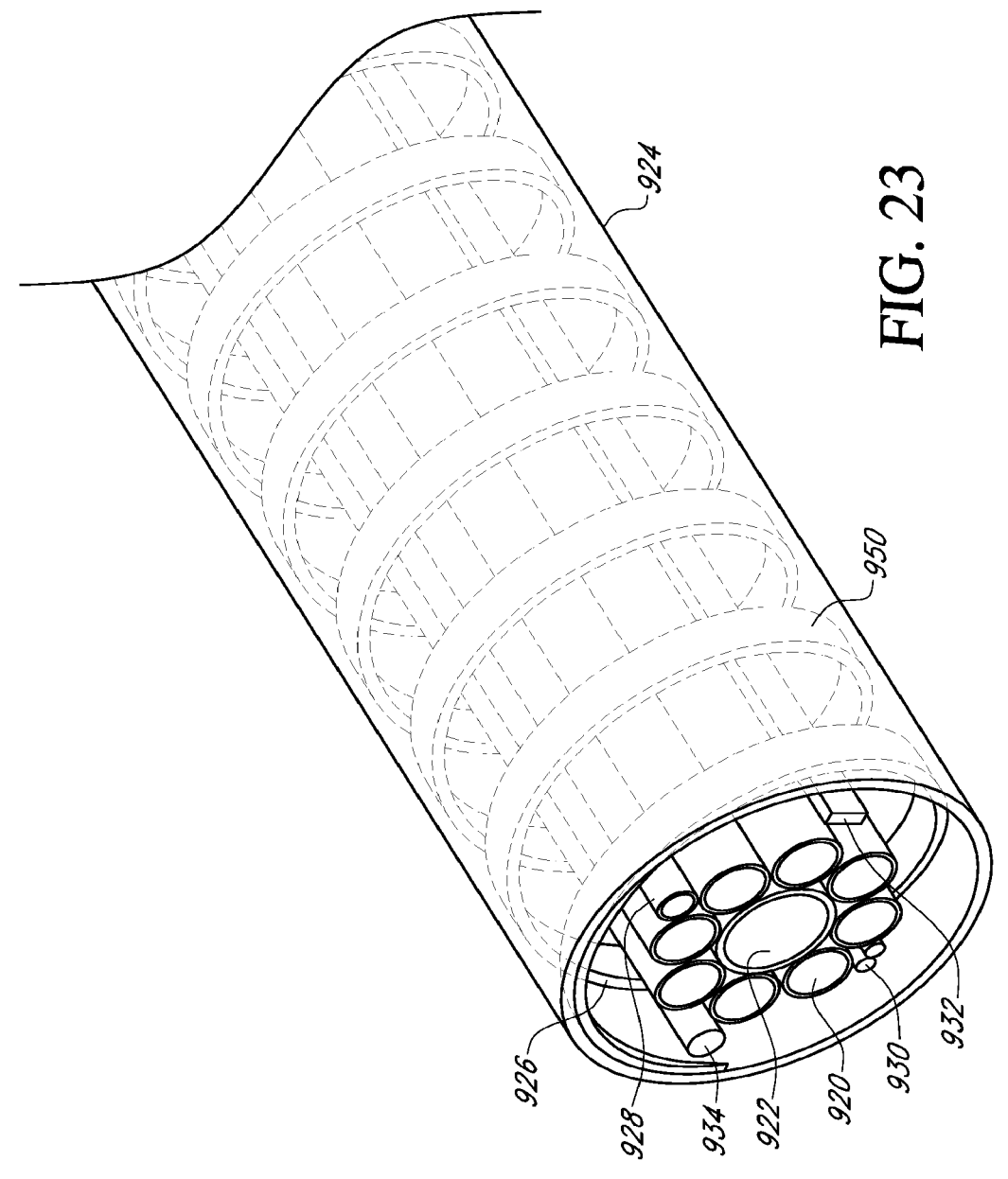
FIG. 23 is an illustration of a distal section of an embodiment of a cryoablation catheter comprising a spring element.

FIG. 23 shows another protective barrier that includes a flexible outer cover 924, and a skeleton 950. Preferably, the cover is flexible and may be articulated. Cover forms a fluid-tight seal around (or otherwise encapsulates) the tube bundle. In embodiments, the cover may bend or deflect but does not expand. The cover is thermally conductive. It may be made of a polymeric material. Examples of suitable polymers for the cover include but are not limited to polyimide. Alternatively, the cover may be made of other materials including metals and alloys such as Nitinol. A relatively thin wall thickness is desirable to increase thermal conductivity between the cryogen and the tissue.

Figure 24:
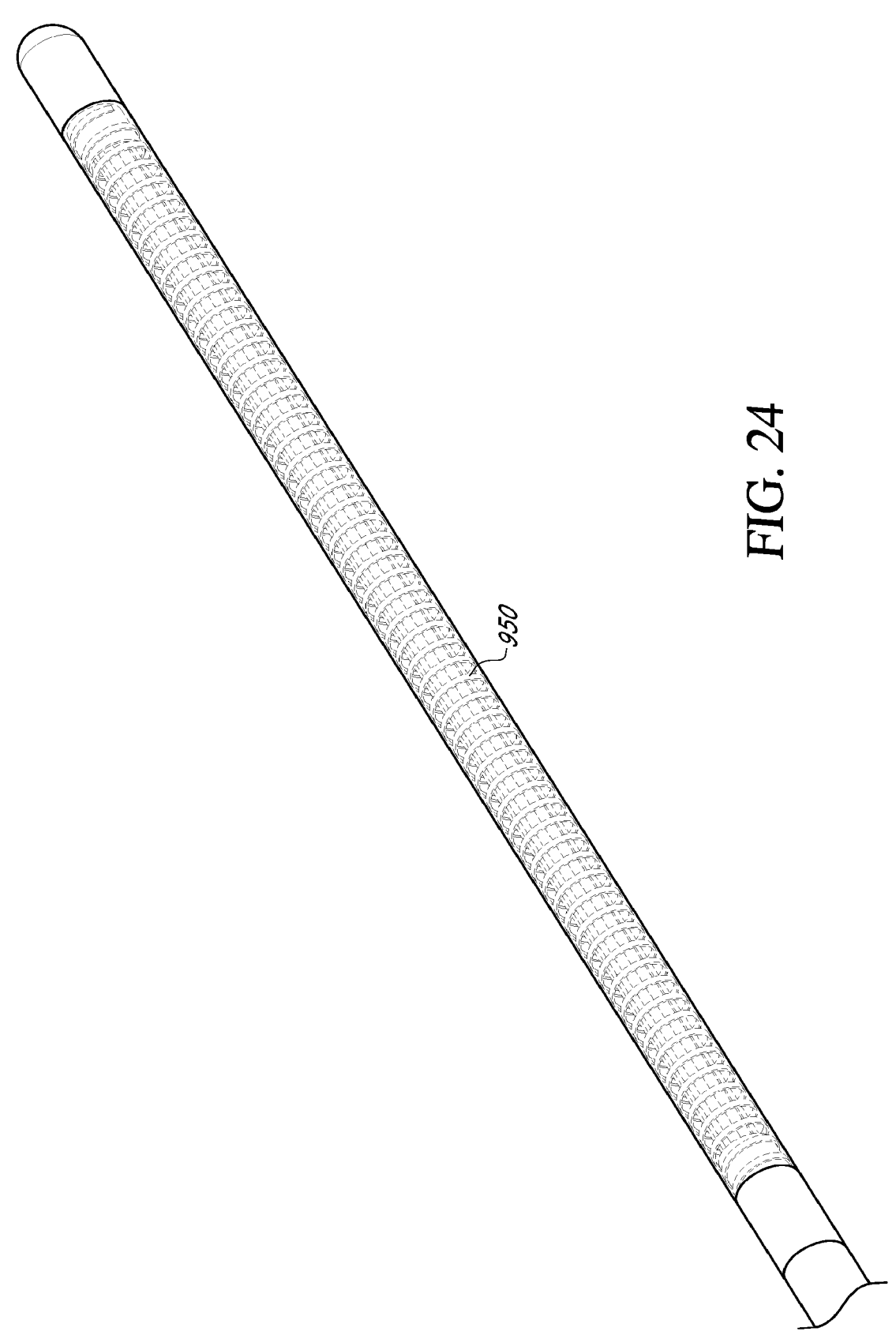
FIG. 24 is a perspective view of a distal section of another embodiment of a cryoablation catheter comprising a spring element.

The skeleton or exoskeleton may comprise a spring or coil member 950 as shown. Spring 950 can be a metal or alloy with sufficient flexibility and elasticity to be navigated through the vasculature and into the heart chambers as will be described in more detail below. The coil may be deflected to take a particular shape and subsequently be capable of being returned to its resting shape. An embodiment of a coil material is annealed stainless steel. For purposes of illustration, FIG. 24 shows a distal section of a catheter with the cover removed. Coil 950 is shown spanning the entire length of the distal treatment section and terminating at the end cap. The coil includes a number of struts and gaps between the struts. However, the shape of the coil may vary and the disclosure is intended only to be limited as recited in the appended claims.

Bellow-Shaped Cover

Figure 25:
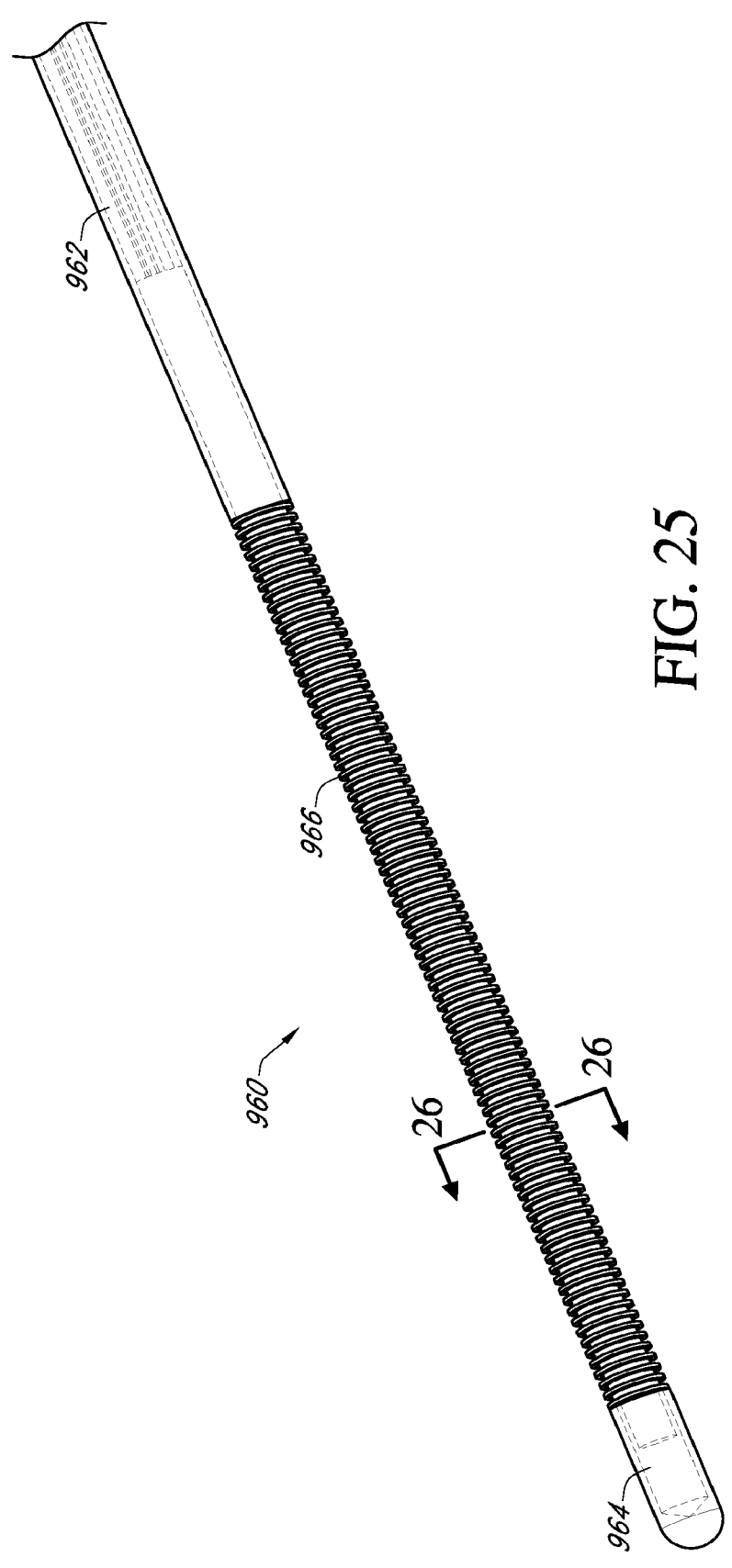
FIG. 25 is a perspective view of a distal section of another embodiment of a cryoablation catheter having an outer cover comprising a bellows element.

FIG. 25 shows another cryoablation catheter 960 comprising a protective cover or exoskeleton 966. In particular, a bellow or corrugated shaped member 966 is shown extending from an intermediate section 962 of the catheter to the distal end 964.

Figure 26:
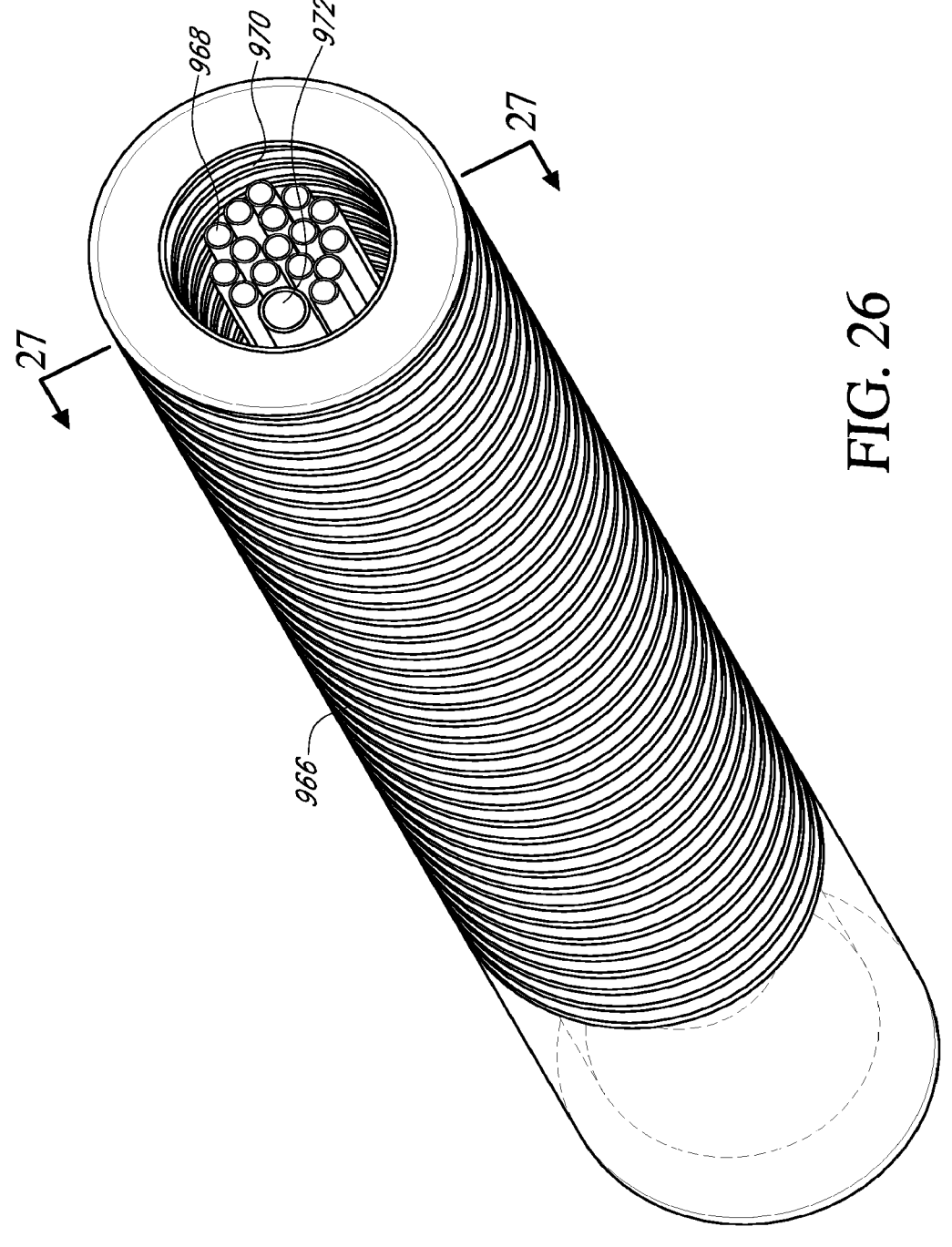
FIG. 26 is a cross sectional view of an embodiment of a catheter shown in FIG. 25 taken along line 26-26.

FIG. 26 shows a cross section of the distal treatment section of the catheter taken along line 26-26. Similar to some of the cryoablation apparatuses described herein, a tube bundle of micro tubes 968 is provided to transport a cooling fluid to and from the treatment section to cool or ablate the tissue.

A space is shown 970 between the tube bundle and the inner surface of the exoskeleton member 966. Space is filled with a thermally conductive liquid or gel as described herein.

Line 972 is shown to provide thermally conductive liquid to the space 970. Gel or media is preferably non-circulating. Gel or thermally conductive liquid is delivered through an inlet port at the proximal end of the catheter, and sealed. Additionally, as described herein, a pressure sensor or gauge may be incorporated in the fluid line to measure pressure or a change in pressure of the thermally conductive fluid. In the event a change of pressure occurs, activation of the cryo-energy is halted.

Figure 27:
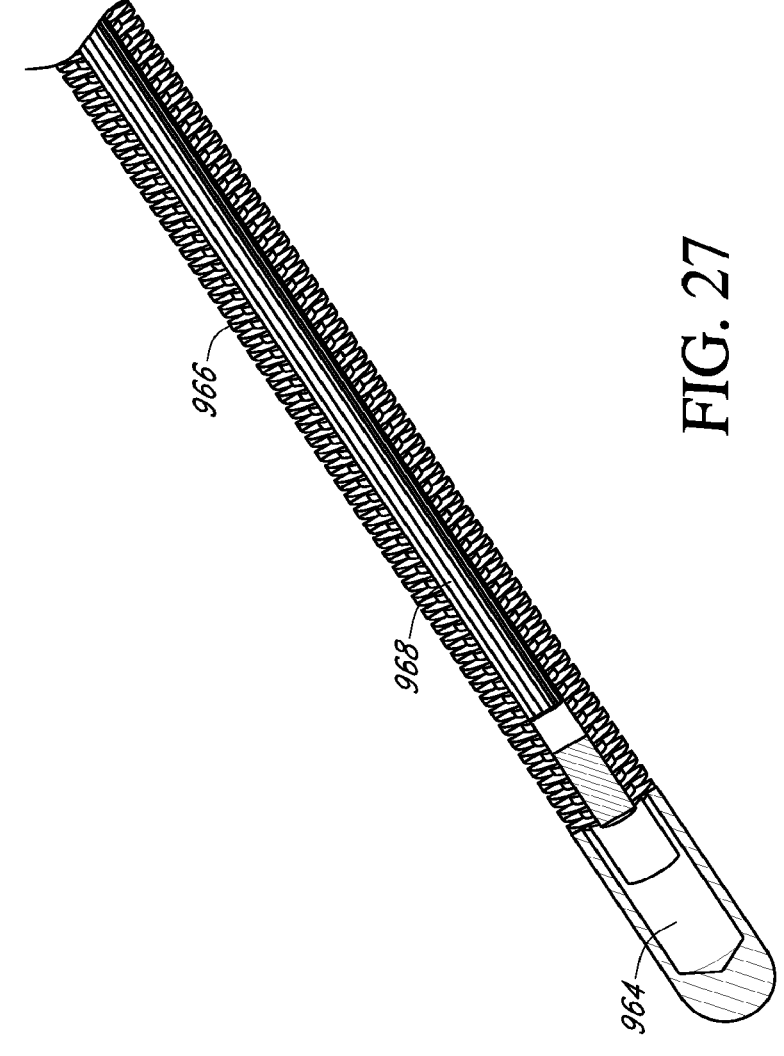
FIG. 27 is a lengthwise sectional view of an embodiment of a catheter shown in FIG. 26 taken along line 27-27.

With reference to FIG. 27, the bellows member 966 extends to the distal tip 964. Bellows 966 circumferentially or coaxially surrounds tube bundle 968 and connects to distal tip 964 or plug member. A fluidly sealed connection between the plug member 964 and bellow may be carried out with an adhesive or other suitable bonding technique.

Tube within Tube

Figure 28:
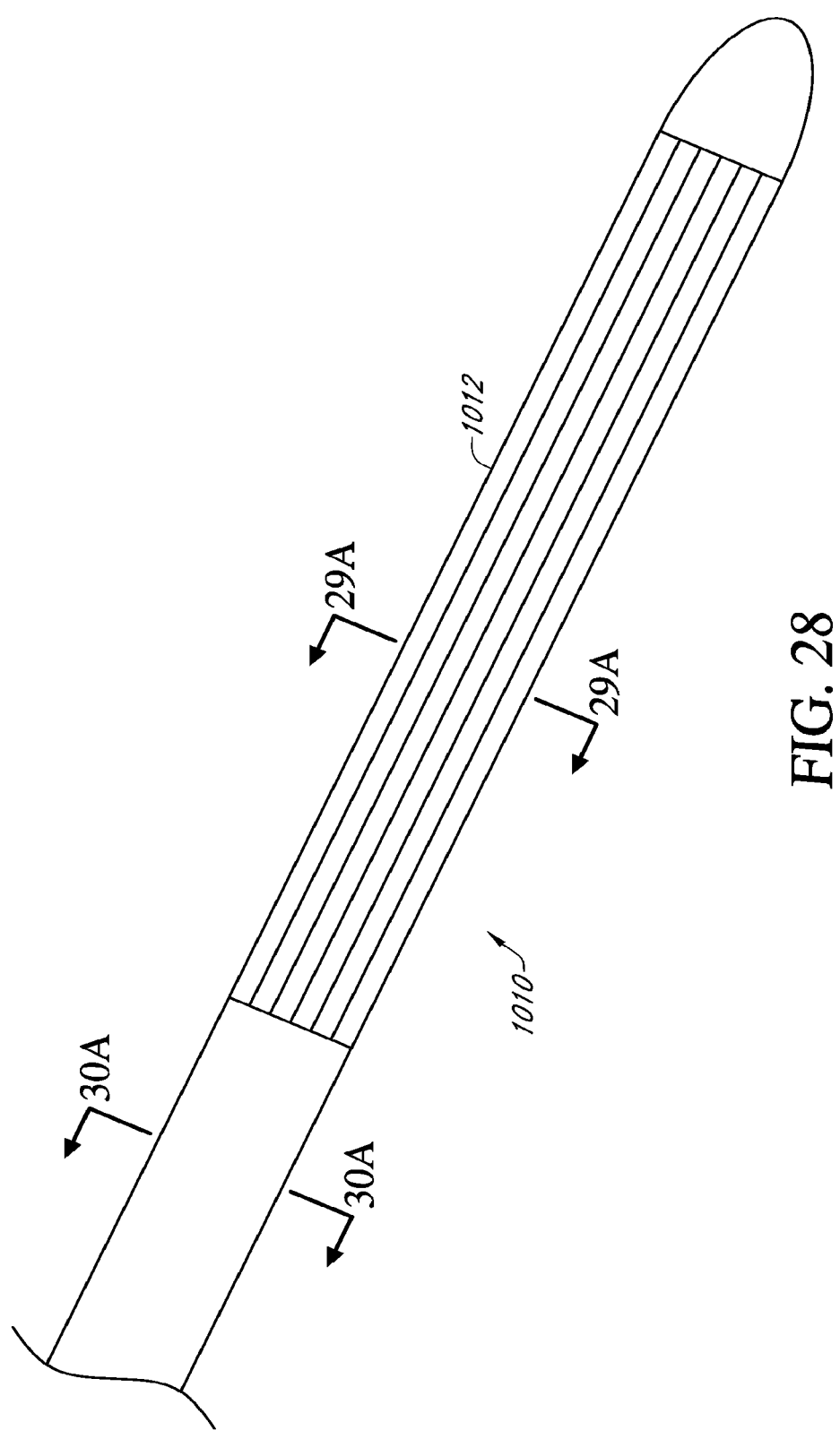
FIG. 28 is a perspective view of another embodiment of a cryoablation catheter having a flexible distal treatment section.

FIG. 28 shows a partial view of another cryoablation catheter 1010 having a protective means to mitigate leaks in the event of a cryogen or cooling liquid leak from the cryoenergy delivery tubes described above.

Figure 29B:
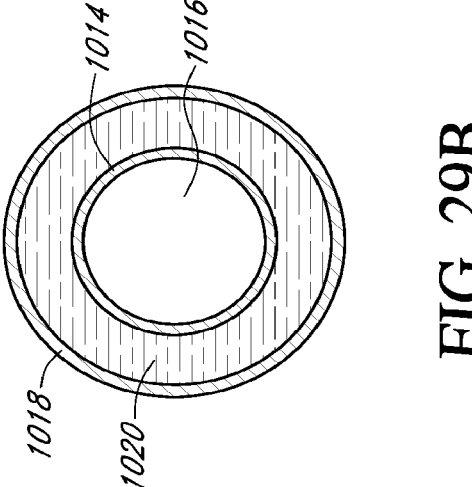
FIG. 29B is an enlarged view of one of the multi-layered tubes shown in FIG. 28A.
Figure 29A:
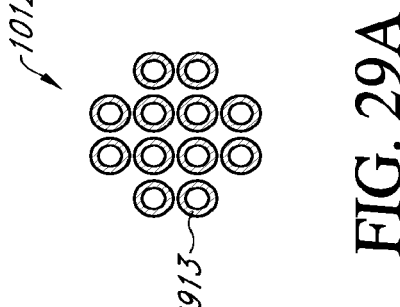
FIG. 29A is a cross sectional view of an embodiment of a catheter shown in FIG. 28 taken along line 29A-29A.

In particular, with reference to FIGS. 29A-29B, catheter 1010 comprises a plurality or bundle of flexible multi-layer cryoenergy transfer tubes 1012, each of which comprises two tubes in a coaxial arrangement, namely a tube within a tube.

FIG. 29B shows an enlarged view of one cryoenergy transfer tube including an inner or first tube 1014 for circulating or transporting a cryogen or cooling liquid 1016 for effecting cryoablation. The first tube 1014 is shown coaxially surrounded by a second or outer tube 1018. A space or gap between the exterior surface of the inner tube and the interior surface of the outer tube 1020 is filled with a thermally conductive media as described herein.

In the event of a leak of the cooling liquid or breach of the inner tube, the cooling liquid is contained within the outer tube 1018.

The inner tube 1014 may be fabricated and made from materials as described herein in connection with other flexible tubes for transporting the cooling fluid.

The outer tube material shall also be flexible to enable elastic deflection of the distal treatment section. Non-limiting exemplary materials for the outer tube 1018 include polymers and metals or alloys. An example of an outer shell material is Nitinol.

As shown in FIG. 29A, a bundle of multilayer tubes 1012 may be assembled in a parallel arrangement. FIG. 29A shows 12 protected tubes 1012, however, the number may vary widely. The profile of the tube bundle may also vary.

FIG. 29A shows a substantially circular profile bundle, however, in embodiments, the arrangement may be rectangular, square, cross, or another shape profile, including some of the arrangements described above. The tubes may be braided or woven.

Additionally, steering elements, sensors and other functional elements as described above may be incorporated into the catheter shown in FIG. 28.

Figure 30A:
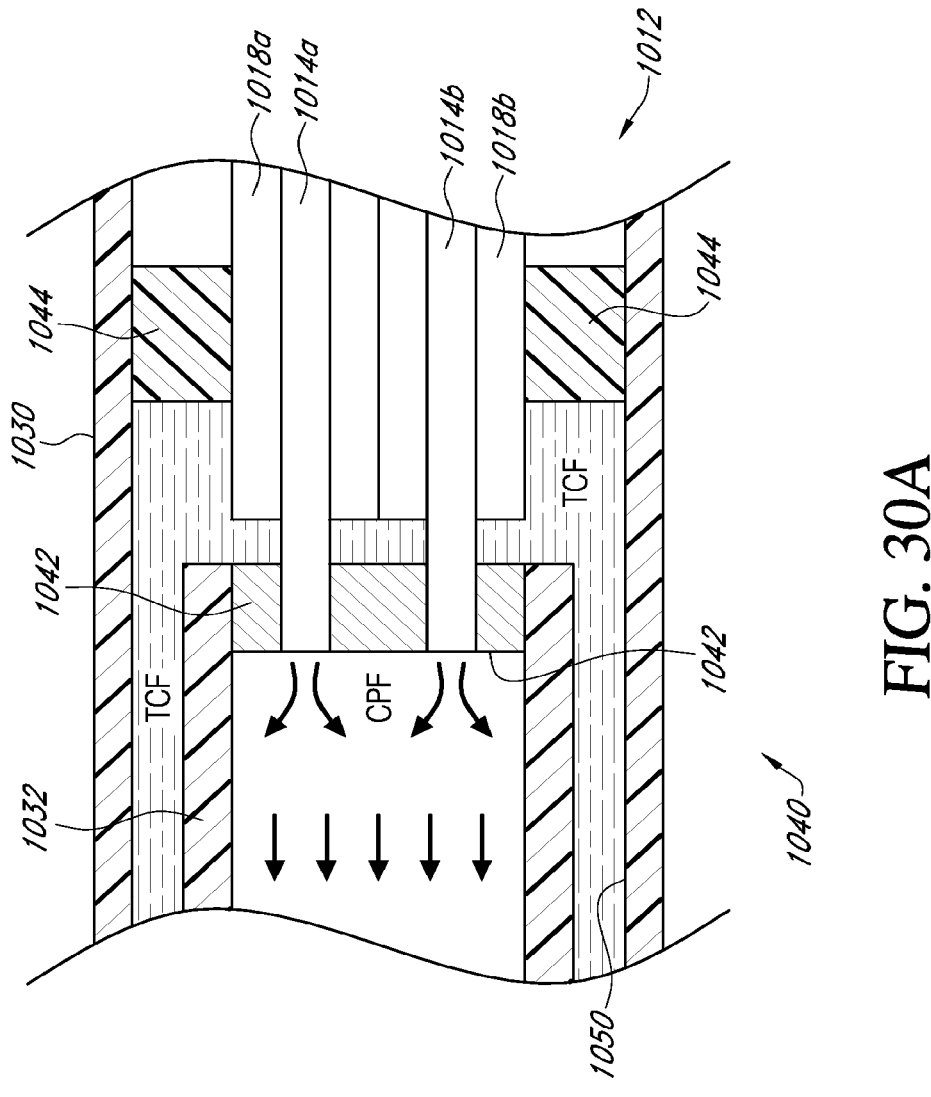
FIG. 30A is a cross sectional view of an embodiment of a catheter shown in FIG. 28 taken along line 30A-30A.

FIG. 30A shows a partial sectional view of the catheter taken along line 30A-30A, illustrating tube bundle 1012 fluidly connected to the end portion 1040 of an intermediate section of the catheter 1010.

Figure 30B:
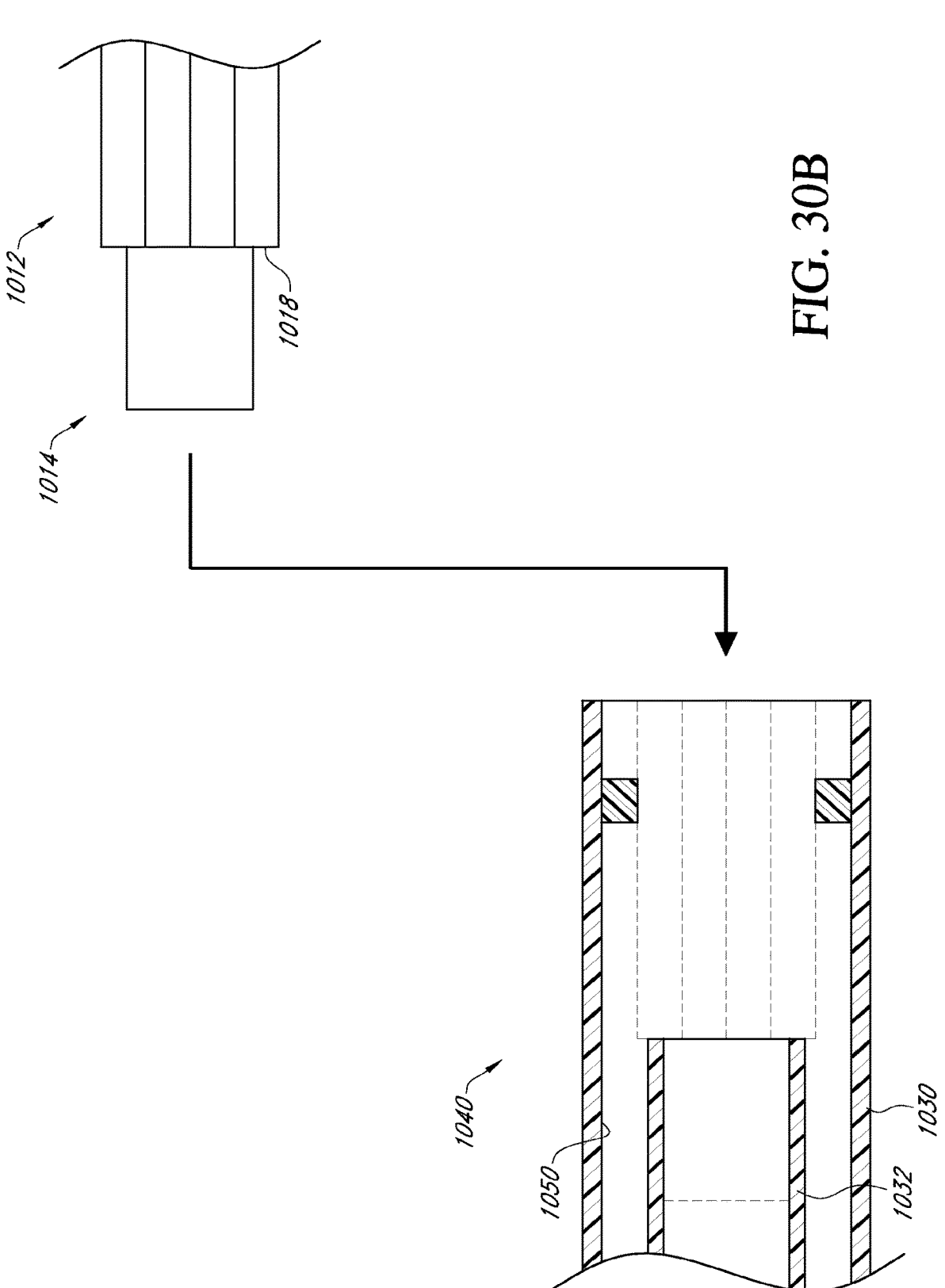
FIG. 30B is a partial exploded view of the proximal ends of the tube elements and the distal end of the intermediate section of an embodiment of a catheter shown in FIG. 28.

FIG. 30B shows an exploded view of a proximal section of the tube bundle 1012 and the intermediate section of catheter 1040. Tube bundle 1012, having inner tubular elements 1014 extending beyond outer covers 1018, can be inserted into intermediate section of catheter 1040.

In particular, and with reference to FIGS. 30A-30B, fluid return lines 1014*a,b* are bundled together and inserted/joined to main return line 1032. An adhesive plug 1042 or seal, gasket, or stopper, etc. may be applied to facilitate and ensure a fluid seal between the tube members. The cooling power fluid (CPF) is transported from the fluid delivery lines 1014*a,b* and into the fluid return main line 1032.

The proximal ends of outer covers 1018*a,b* which are offset from proximal ends of inner lines 1014*a,b*, are shown inserted into intermediate section 1040 of catheter such that the thermally conductive fluid (TCF) within lumen 1050 can fill gaps 1020 (FIG. 29B) of each of the multi-layer cryo-energy transfer tubes 1012. An adhesive plug 1044 or weld or bond may be applied to facilitate a fluid tight and robust connection. Press fits, heat, and other fabrication techniques can be applied to join components as is known to those of skill in the art.

Applications

The ability to have a safe leak proof flexible cryoablation apparatus extends cryotherapy from a rigid needle-like application to a wide range of diagnostic and therapeutic procedures. An exemplary application is endovascular based cardiac ablation to create elongate continuous lesions. As described herein, creating elongate continuous lesions in certain locations of the heart can serve to treat various conditions such as, for example, atrial fibrillation.

The Cox maze procedure to treat atrial fibrillation has been performed using radio frequency ablation catheters in both transthoracic epicardial approaches and transvascular endocardial approaches.

In transthoracic epicardial approaches, catheters or small probes are used to create linear lesions in the heart wall along lines corresponding to the maze of the Cox maze procedure. In the transvascular endocardial approaches, a catheter is navigated through the vasculature of the patient to the atrium, pressed against the inner wall of the atrium, and energized to create lesions corresponding to the maze of the Cox maze procedure.

Figure 31:
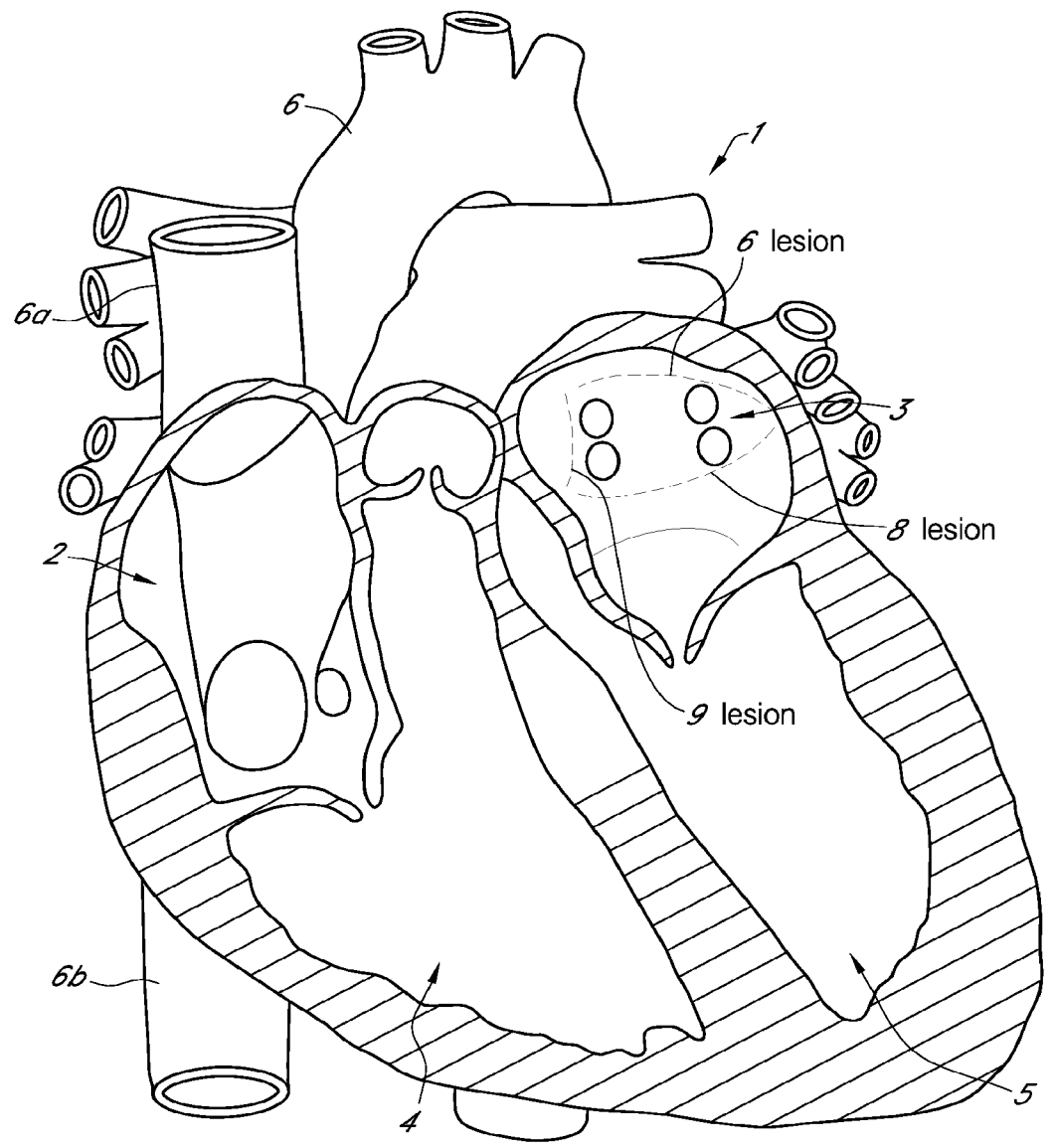
FIG. 31 is an illustration of a heart, and locations of various lesions according to some embodiments.

FIG. 31 shows examples of target sections of tissue and lesions in a Cox Maze procedure. Basic structures of the heart include the right atrium 2, the left atrium 3, the right ventricle 4 and the left ventricle 5. Catheters may be inserted into these chambers of the heart through various vessels, including the aorta 6 (accessed through the femoral artery), the superior vena cava 6*a* (accessed through the subclavian veins) and the inferior vena cava 6*b* (accessed through the femoral vein).

The following discussion will focus on embodiments for performing the left atrium lesion of the Cox maze VII procedure, but the procedure for producing these lesions can be used to create other lesions in an around the heart and other organs. Additional lesions of the Cox maze VII procedure, as well as other variations of the Cox Maze treatments may be carried out using steps and devices described herein. Additional techniques and devices are described in international patent application nos. PCT/US2012/047484 to Cox et al. and PCT/US2012/047487 to Cox et al. corresponding to International Publication Nos. WO 2013/013098 and WO 2013/013099 respectively, the entirety of each of which is hereby incorporated by reference in their entirety.

In FIG. 31, a few of the left atrium lesions of the Cox maze VII lesion are illustrated. Cox maze lesions 6, 8 and 9 are shown on the inner wall of the left atrium. These correspond to the superior left atrial lesion (item 6) spanning the atrium over the left and right superior pulmonary vein entries into the atrium, the inferior left atrial lesion (item 8) spanning the atrium under the left and right inferior pulmonary vein entries into the atrium, and the vertical lesion (item 9) connecting the superior left atrial lesion and inferior left atrial lesion so that the right pulmonary veins are within the area defined by the lesions.

Figure 32:
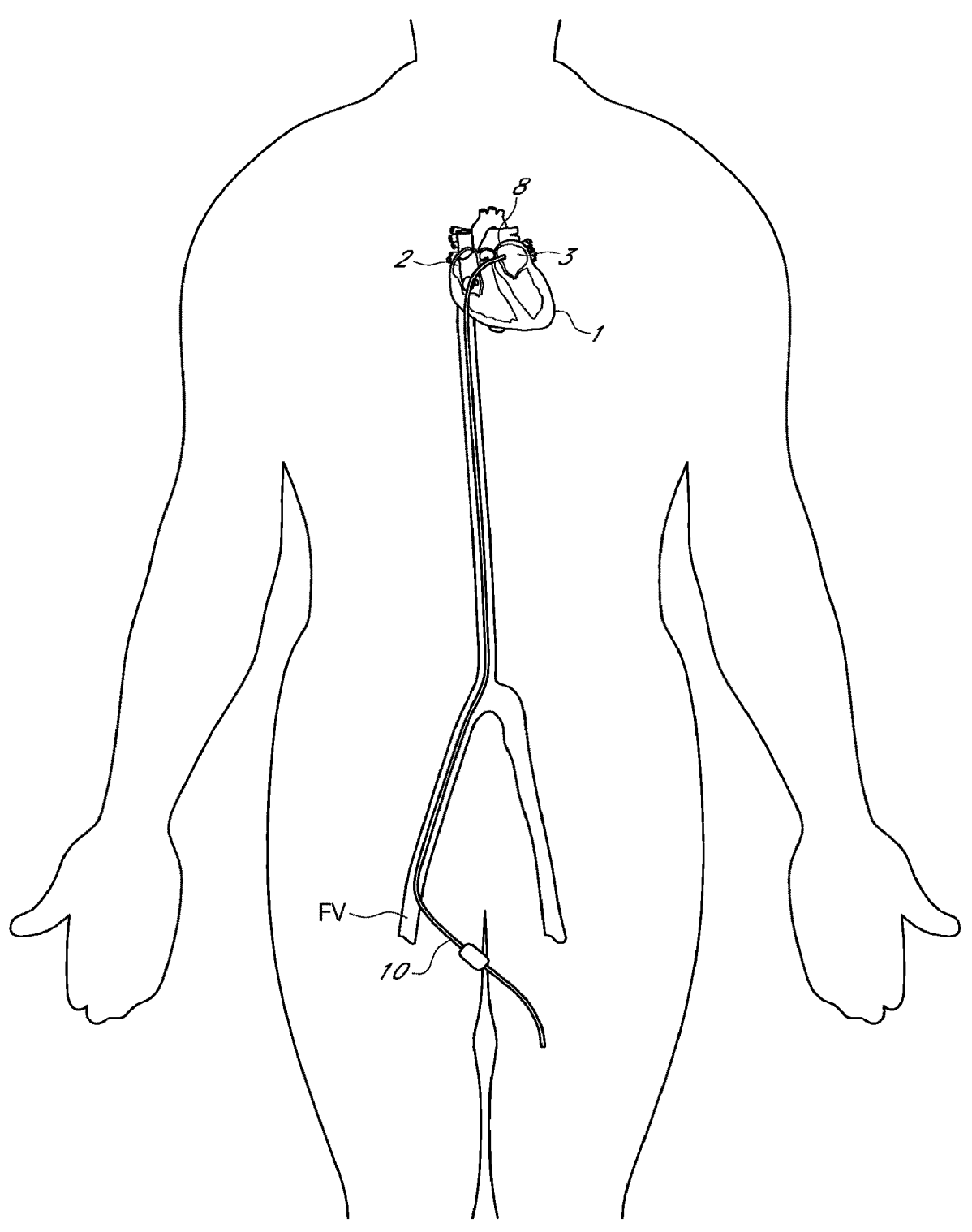
FIG. 32 is an illustration of an embodiment of endovascular catheterization to access the heart.

FIG. 32 illustrates one technique to reach the left atrium with the distal treatment section of a catheter. A peripheral vein (such as the femoral vein FV) is punctured with a needle. The puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter 10 or sheath is introduced through the hemostatic valve of the introducer sheath and is advanced along the peripheral vein, into the target heart region (e.g., the vena cavae, and into the right atrium 2). Fluoroscopic imaging can be used to guide the catheter to the selected site.

Once in the right atrium 2, the distal tip of the guiding catheter is positioned against the fossa ovalis in the intraatrial septal wall. A needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for devices through its own inner lumen and into the left atrium.

Other left atrial access methods may be suitable substitutes for using the ablation device assembly of the present disclosure. In one alternative, a "retrograde" approach may be used, wherein the guiding catheter is advanced into the left atrium from the arterial system. In this variation, the Seldinger technique may be employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Figure 33:
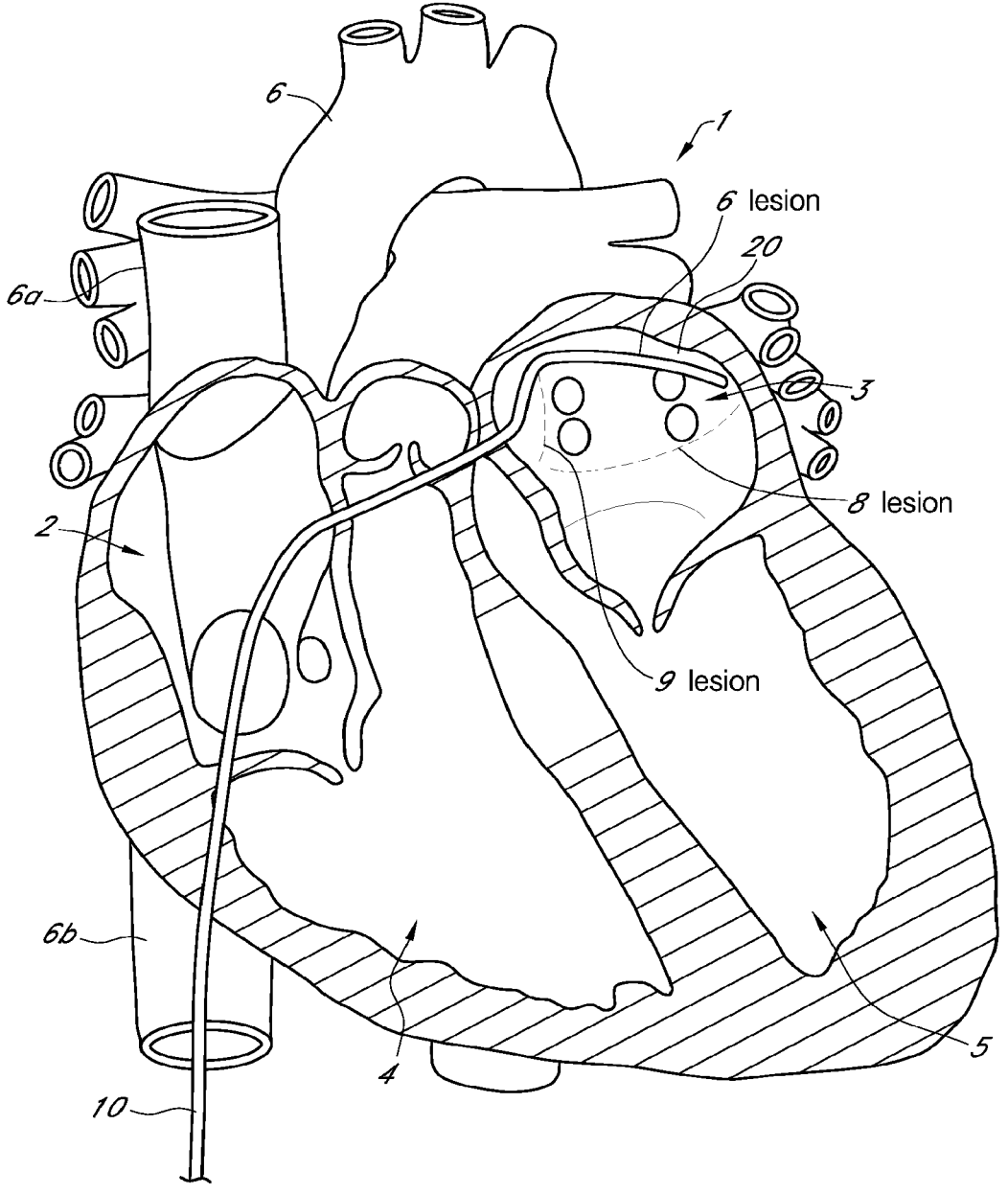
FIG. 33 is an illustration of a distal section of an embodiment of a cryoablation catheter placed in a chamber of the heart.

As shown in FIG. 33, an endocardial catheter 20 advanced through the guide catheter 10 establishes the desired line of a lesion of the left atrium. The distal segment of the endocardial catheter 20 is steerable so that it can be deflected within the endocardial space of the atrium and held firmly against the endocardial wall of the left atrium, and may be relatively stiff and non-compliant with the heart wall. This is illustrated in FIG. 33, where the distal treatment section has been configured and deflected to cover the superior left atrial lesion 6.

An exemplary lesion has a length ranging from 2-10 cm., and more preferably between 5-8 cm.

In embodiments, the device and method is adapted and intended to create a lesion 1) spanning the atrium over the left and right superior pulmonary vein entries into the atrium, 2) under the left and right inferior pulmonary vein entries into the atrium and/or 3) a vertical lesion on the right of the right superior and inferior vein entries into the atrium. The lesions are preferably continuous and linear, not a series of spots such as in some prior art point-ablation techniques. In accordance with the designs described above, the cryo-energy and heat transfer is focused on the endocardium, and intended to create the lesion completely through the endocardium.

Additionally, in embodiments, catheters achieve cooling power without vapor lock by transporting the cooling fluid near its critical point in the phase diagram. Additionally, in embodiments, catheters achieve such cooling power despite having a protective cover or redundant shell to contain any cryogen leaks. The distal treatment section designs described herein are intended for creating elongate continuous lesions spanning the full thickness of the heart wall, and in a safe manner to mitigate collateral damage in the event of a cryogen leak. The heat sink associated with the warm blood flow through the chambers of the heart is mitigated or avoided altogether because the ablation catheter is positioned within the heart chamber and directs the treating energy from the endocardium to the pericardium, or from the inside out.

Multiple endovascular products are described herein having a) pressures of near-critical nitrogen below the maximum tolerance of ~600 psi for endovascular catheter material, and b) dangers arising from leaks contained. A cardiac ablation catheter in accordance with the principals of the present disclosure can be placed in direct contact along the internal lining of the left atrium, thereby avoiding most of the massive heat-sink of flowing blood inside the heart as the ablation proceeds outward.

Additionally, catheter configurations include substantial bends, or loops which provide both the circumferential, as well as linear, ablations to mimic the surgical Maze procedure noted above. The catheters described herein may be manipulated to form ring shaped lesions near or around the pulmonary vessel entries, for example.

The devices described herein may have a wide variety of applications including, for example, endoscopic cryotherapy. Candidate tumors to be ablated with cryoenergy include target tissues and tumors in the bronchial tree or lung as well as tissues in the upper and lower GI. The devices described herein may also be applied to destroy or limit target tissues in the head and neck.

Many modifications and variations of the present disclosure are possible in light of the above teachings. It is, therefore, to be understood that within the scope of the appended claims, the disclosure may be practiced otherwise than as specifically described.

What is claimed is:

1. An endovascular near critical Nitrogen based cryoablation system for creating a lesion along an interior wall of the heart, the system comprising:
    a near critical Nitrogen pressure generator;
    a near critical Nitrogen cooler for cooling a near critical Nitrogen;
    a near critical Nitrogen based endovascular cryoablation catheter in fluid communication with the generator; and
    a controller operable to modify a flow rate of the near critical Nitrogen thereby controlling an ablative power delivered from a distal treatment section of the catheter to the interior wall of the heart, wherein the distal treatment section is configured to create a continuous transmural lesion of about 2 cm to about 10 cm in length.

2. The system of claim 1 further comprising a timer to signal when to stop delivering ablative power.

3. The system of claim 1 wherein the distal treatment section of the catheter includes an outer, flexible, cover and a thermally conductive media disposed therein.

4. The system of claim 3 further comprising a pressure sensor for sensing a fluid pressure of the thermally conductive media, and the controller being operable to halt the delivery based on the thermally conductive media fluid pressure.

5. The system of claim 3 further comprising a temperature sensor for sensing a fluid temperature of the thermally conductive media, and the controller being operable to halt the delivery based on the thermally conductive media fluid temperature.

6. The system of claim 3 further comprising a flexible guide sheath, through which the cryoablation catheter is advanceable.

7. The system of claim 1, wherein the distal treatment section of the catheter includes a bundle of fluid paths for delivering the near critical nitrogen to and from the distal tip, and to the wall of the heart.

8. The system of claim 7, wherein the distal treatment section of the catheter includes an endcap.

9. The system of claim 1, wherein the catheter further comprises a pull wire to deflect or steer the catheter.

10. The system of claim 1, further comprising a console within which the generator, cooler, and controller are arranged.

* * * * *